United States Patent
Totsu et al.

(10) Patent No.: US 10,467,747 B2
(45) Date of Patent: Nov. 5, 2019

(54) IMAGE ANALYSIS APPARATUS, IMAGING SYSTEM, SURGERY SUPPORT SYSTEM, IMAGE ANALYSIS METHOD, STORAGE MEDIUM, AND DETECTION SYSTEM

(71) Applicant: NIKON CORPORATION, Minato-ku, Tokyo (JP)

(72) Inventors: Masahiro Totsu, Tokyo (JP); Takeshi Hataguchi, Tokyo (JP)

(73) Assignee: NIKON CORPORATION, Tokyo (JP)

( * ) Notice: Subject to any disclaimer, the term of this patent is extended or adjusted under 35 U.S.C. 154(b) by 83 days.

(21) Appl. No.: 15/402,385

(22) Filed: Jan. 10, 2017

(65) Prior Publication Data
US 2017/0148164 A1 May 25, 2017

Related U.S. Application Data

(63) Continuation of application No. PCT/JP2014/068629, filed on Jul. 11, 2014.

(51) Int. Cl.
*G06T 7/00* (2017.01)
*G01N 21/27* (2006.01)
(Continued)

(52) U.S. Cl.
CPC .......... *G06T 7/0012* (2013.01); *A61B 5/0082* (2013.01); *A61B 10/0041* (2013.01);
(Continued)

(58) Field of Classification Search
CPC .. G01N 21/27; G01N 21/359; G01N 21/4738; G01N 2021/3129;
(Continued)

(56) References Cited

U.S. PATENT DOCUMENTS

| 4,143,401 A * | 3/1979 | Coviello | G06T 9/20 |
| | | | 348/26 |
| 5,711,755 A * | 1/1998 | Bonnell | A61B 1/042 |
| | | | 250/353 |

(Continued)

FOREIGN PATENT DOCUMENTS

| JP | 2003-503135 A | 1/2003 |
| JP | 2006-102360 A | 4/2006 |

(Continued)

OTHER PUBLICATIONS

Japanese Office Action dated Apr. 16, 2018 as issued in corresponding Application No. 2016-532397 with English Translation thereof.

*Primary Examiner* — Mekonen T Bekele
(74) *Attorney, Agent, or Firm* — Foley & Lardner LLP

(57) ABSTRACT

An image analysis apparatus includes: a distribution data generator that generates, on the basis of a sample image obtained by irradiating a biological tissue with light having an infrared bandwidth, distribution data indicating a distribution of light intensity in the infrared bandwidth in the tissue; a differential calculator that calculates, on the basis of the distribution data, an Nth-order derivative of the distribution of the light intensity in a first wavelength band in the infrared bandwidth, where N is an integer of 2 or more, for each region in the sample image; and an image data generator that converts the Nth-order derivative into a grayscale value to generate image data.

30 Claims, 12 Drawing Sheets

(51) Int. Cl.
    *G01N 21/359* (2014.01)
    *A61B 5/00* (2006.01)
    *G06K 9/00* (2006.01)
    *G06K 9/46* (2006.01)
    *A61B 10/00* (2006.01)
    *G01N 21/47* (2006.01)
    *G06K 9/20* (2006.01)
    *G01N 21/31* (2006.01)

(52) U.S. Cl.
    CPC ........... *G01N 21/27* (2013.01); *G01N 21/359* (2013.01); *G01N 21/4738* (2013.01); *G06K 9/0014* (2013.01); *G06K 9/00134* (2013.01); *G06K 9/4609* (2013.01); *G06K 9/4647* (2013.01); *A61B 5/0077* (2013.01); *G01N 2021/3129* (2013.01); *G06K 9/2018* (2013.01); *G06T 2207/10048* (2013.01); *G06T 2207/10056* (2013.01); *G06T 2207/10152* (2013.01); *G06T 2207/30016* (2013.01); *G06T 2207/30024* (2013.01)

(58) Field of Classification Search
    CPC ............. G06K 9/00134; G06K 9/0014; G06K 9/4609; G06K 9/4647; G06K 9/2018; G06T 7/0012; G06T 2207/10048; G06T 2207/10056; A61B 10/0041; A61B 5/0082; A61B 5/0077
    See application file for complete search history.

(56) References Cited

U.S. PATENT DOCUMENTS

| | | | | |
|---|---|---|---|---|
| 5,833,596 | A | * | 11/1998 | Bonnell ................ A61B 1/042 600/109 |
| 6,990,364 | B2 | * | 1/2006 | Ruchti ............... A61B 5/14532 600/310 |
| 9,002,439 | B2 | | 4/2015 | Okada et al. |
| 2004/0068163 | A1 | * | 4/2004 | Ruchti ............... A61B 5/14532 600/316 |
| 2004/0127777 | A1 | | 7/2004 | Ruchti et al. |
| 2004/0236229 | A1 | | 11/2004 | Freeman et al. |
| 2007/0027362 | A1 | | 2/2007 | Handa et al. |
| 2007/0290969 | A1 | * | 12/2007 | Hsu ..................... G09G 3/3696 345/89 |
| 2010/0220907 | A1 | * | 9/2010 | Dam ....................... G06K 9/34 382/131 |
| 2011/0168895 | A1 | | 7/2011 | Nagai et al. |
| 2011/0295062 | A1 | | 12/2011 | Gratacos Solsona et al. |
| 2012/0078117 | A1 | * | 3/2012 | Okada ................. A61B 5/0075 600/476 |
| 2012/0082362 | A1 | | 4/2012 | Diem et al. |
| 2012/0328178 | A1 | | 12/2012 | Remiszewski et al. |
| 2013/0343071 | A1 | * | 12/2013 | Nagaoka ............... B60Q 9/008 362/466 |
| 2016/0091707 | A1 | | 3/2016 | Okuno et al. |
| 2016/0110584 | A1 | * | 4/2016 | Remiszewski ........ G06T 7/0012 382/133 |
| 2018/0238796 | A1 | * | 8/2018 | Cooke ................... D06F 39/003 |

FOREIGN PATENT DOCUMENTS

| | | |
|---|---|---|
| JP | 2007-075366 A | 3/2007 |
| JP | 2007-075445 A | 3/2007 |
| JP | 2008-132335 A | 6/2008 |
| JP | 2009-512500 A | 3/2009 |
| JP | 2009-168670 A | 7/2009 |
| JP | 2010-074099 A | 4/2010 |
| JP | 2010-217149 A | 9/2010 |
| JP | 2012-511361 A | 5/2012 |
| JP | 2012-202718 A | 10/2012 |
| JP | 2012202718 A * | 10/2012 |
| JP | 2013-535014 A | 9/2013 |
| JP | 2014-236911 A | 12/2014 |
| JP | 2015-102542 A | 6/2015 |
| WO | WO-2007/046983 A2 | 4/2007 |
| WO | WO-2010/131697 A1 | 11/2010 |
| WO | WO-2010/131713 A1 | 11/2010 |

* cited by examiner

FIG. 3

$$d1(\lambda_n) = \frac{I(\lambda_{n+1}) - I(\lambda_n)}{\lambda_{n+1} - \lambda_n} \quad \cdots \text{EXPRESSION (1)}$$

$$d2(\lambda_n) = \frac{d1(\lambda_{n+1}) - d1(\lambda_n)}{\lambda_{n+1} - \lambda_n} \quad \cdots \text{EXPRESSION (2)}$$

$$d1(\lambda_n) = \frac{I(\lambda_{n+1}) - I(\lambda_{n-1})}{\lambda_{n+1} - \lambda_{n-1}} \quad \cdots \text{EXPRESSION (3)}$$

$$d1(\lambda_n) = \frac{I(\lambda_n) - I(\lambda_{n-1})}{\lambda_n - \lambda_{n-1}} \quad \cdots \text{EXPRESSION (4)}$$

$$d2(\lambda_n) = \frac{d1(\lambda_{n+1}) - d1(\lambda_{n-1})}{\lambda_{n+1} - \lambda_{n-1}} \cdots \text{EXPRESSION (5)}$$

$$d2(\lambda_n) = \frac{d1(\lambda_n) - d1(\lambda_{n-1})}{\lambda_n - \lambda_{n-1}} \quad \cdots \text{EXPRESSION (6)}$$

$$I(\lambda) = \sum_{i=0}^{N} C_i \lambda^i \quad \cdots \text{ EXPRESSION (7)}$$

$$d2(\lambda n) = \sum_{i=2}^{N} i(i-1) C_i \lambda_n^{i-2} \quad \cdots \text{ EXPRESSION (8)}$$

IMAGE ANALYSIS APPARATUS, IMAGING SYSTEM, SURGERY SUPPORT SYSTEM, IMAGE ANALYSIS METHOD, STORAGE MEDIUM, AND DETECTION SYSTEM

CROSS REFERENCE TO RELATED APPLICATION

This is a Continuation of PCT Application No. PCT/JP2014/068629, filed on Jul. 11, 2014. The contents of the above-mentioned application are incorporated herein by reference.

FIELD OF THE INVENTION

The present invention relates to an image analysis apparatus, an imaging system, a surgery support system, an image analysis method, A storage medium, and a detection system.

BACKGROUND

In medical and other fields, a technology of capturing an image of a biological tissue and utilizing the image for various kinds of diagnosis, tests, and observation is proposed (see, for example, Patent Literature 1). The apparatus according to Patent Literature 1 is, for example, a technology of irradiating a body tissue with infrared rays and acquiring an image of subcutaneous vessels on the basis of the infrared rays reflected by the body tissue.

CITATION LIST

Patent Literature

[Patent Literature 1] Japanese Unexamined Patent Application Publication No. 2006-102360

It is expected for the above-described technology to accurately obtain information on a biological tissue. For example, an apparatus that analyzes a sample image in which a tissue is captured is required to accurately distinguish a particular part from other parts in the tissue. The present invention has been made in view of the above-described circumstances, and it is an object thereof to provide an image analysis apparatus, an imaging system, a surgery support system, an image analysis method, A storage medium, and a detection system that are capable of accurately obtaining information on a biological tissue.

SUMMARY

A first aspect of the present invention provides an image analysis apparatus including: a distribution data generator that generates, on the basis of a sample image obtained by irradiating a biological tissue with light having an infrared bandwidth, distribution data indicating a distribution of light intensity in the infrared bandwidth in the tissue; a differential calculator that calculates, on the basis of the distribution data, an Nth-order derivative of the distribution of the light intensity in a first wavelength band in the infrared bandwidth, where N is an integer of 2 or more, for each region in the sample image; and an image data generator that converts the Nth-order derivative into a gray-scale value to generate image data.

A second aspect of the present invention provides an imaging system including: the image analysis apparatus in the first aspect; and an imaging unit that acquires the sample image in the tissue.

A third aspect of the present invention provides an imaging system including: a light source that is capable of outputting at least three infrared light beams having different wavelengths to a biological tissue; a light detector that receives the three infrared light beams via the tissue; and an image analysis apparatus, the image analysis apparatus including: a distribution data generator that generates, on the basis of a sample image obtained from the light detector, distribution data indicating a spectrum of the tissue with the three infrared light beams; a differential calculator that calculates an Nth-order derivative (N is an integer of 2 or more) of the spectrum on the basis of the distribution data; and an image data generator that converts the Nth-order derivative into a gray-scale value to generate image data.

A fourth aspect of the present invention provides a surgery support system including: the imaging system in the second aspect; and an operation device that is capable of treating a tissue.

A fifth aspect of the present invention provides an image analysis method including: generating, on the basis of a sample image obtained by irradiating a biological tissue with light having an infrared bandwidth, distribution data indicating a distribution of light intensity in the infrared bandwidth in the tissue; calculating, on the basis of the distribution data, an Nth-order derivative of the distribution of the light intensity in a first wavelength band in the infrared bandwidth, where N is an integer of 2 or more, for each region in the sample image; and converting the Nth-order derivative into a gray-scale value to generate image data.

A sixth aspect of the present invention provides a storage medium storing therein an image analysis program that causes a computer to execute: generating, on the basis of a sample image obtained by irradiating a biological tissue with light having an infrared bandwidth, distribution data indicating a distribution of light intensity in the infrared bandwidth in the tissue; calculating, on the basis of the distribution data, an Nth-order derivative of a distribution of the light intensity in a first wavelength band in the infrared bandwidth, where N is an integer of 2 or more, for each region in the sample image; and converting the Nth-order derivative into a gray-scale value to generate image data.

A seventh aspect of the present invention provides an image analysis apparatus including: a data generator that generates, on the basis of a detection result obtained by irradiating a target including a first part containing water and a second part containing lipid with infrared light, spectrum data indicating a spectrum of the target; a differential calculator that calculates, on the basis of the spectrum data, an Nth-order derivative (N is an integer of 2 or more) of a spectrum in a predetermined wavelength band that includes a non-linear part of the spectrum, for each of the first part and the second part; and an image data generator that generates, in accordance with the Nth-order derivative for the first part and the Nth-order derivative for the second part, image data in which the first part containing the water or the second part containing the lipid is emphasized.

A eighth aspect of the present invention provides a detection system including: the image analysis apparatus of the seventh aspect and a detector that acquires the detection result.

A ninth aspect of the present invention provides a surgery support system including: the detection system of the eighth aspect; and a display that displays the image data.

A tenth aspect of the present invention provides an image analysis method including: generating, on the basis of a detection result obtained by irradiating a target including a first part containing water and a second part containing lipid with infrared light, spectrum data indicating a spectrum of the target; calculating, on the basis of the spectrum data, an Nth-order derivative (N is an integer of 2 or more) of a spectrum in a predetermined wavelength band that includes a non-linear part of the spectrum, for each of the first part and the second part; and generating, in accordance with the Nth-order derivative for the first part and the Nth-order derivative for the second part, image data in which the first part containing the water or the second part containing the lipid is emphasized.

A eleventh aspect of the present invention provides a storage medium storing therein a program that causes a computer to execute: generating, on the basis of a detection result obtained by irradiating a target including a first part containing water and a second part containing lipid with infrared light, spectrum data indicating a spectrum of the target; calculating, for each of the first part and the second part, on the basis of the spectrum data, an Nth-order derivative (where N is an integer of 2 or more) of a spectrum in a predetermined wavelength band including a non-linear part of the spectrum; and generating, in accordance with an Nth-order derivative at the first part and an Nth-order derivative at the second part, image data in which the first part containing the water or the second part containing the lipid is emphasized.

According to the present invention, an image analysis apparatus, an imaging system, a surgery support system, an image analysis method, A storage medium, and a detection system that are capable of accurately obtaining information on a biological tissue can be provided.

BRIEF DESCRIPTION OF DRAWINGS

FIG. 3 shows an example of expressions used to calculate Nth-order derivatives in the present embodiment.

DETAILED DESCRIPTION OF EMBODIMENTS

First Embodiment

Figure 1:
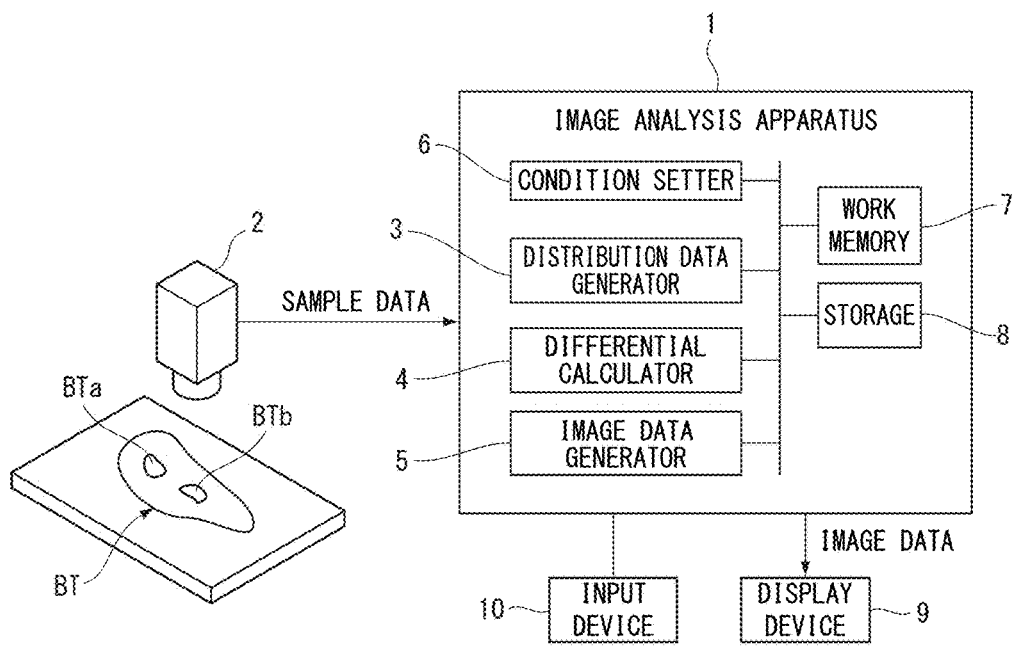
FIG. 1 is a diagram showing an image analysis apparatus according to the present embodiment.

FIG. 1 is a diagram showing an image analysis apparatus 1 according to the present embodiment. Prior to description of each part in the image analysis apparatus 1, the outline of image processing by the image analysis apparatus 1 will be described. For example, the image analysis apparatus 1 analyzes a sample image obtained by irradiating a biological tissue BT with light having an infrared bandwidth, and detects a part of the tissue BT that satisfies a predetermined condition. For example, the predetermined condition includes at least one of the condition that a composition contains a predetermined substance, the condition that the amount of a predetermined substance contained in a composition is a threshold or more, the condition that the amount of a predetermined substance contained in a composition is a threshold or less, or the condition that a composition of one part in the tissue BT differs from that of another part in the tissue BT. For example, the image analysis apparatus 1 determines a distribution of a predetermined substance in the tissue BT, and generates image data indicating the distribution of the predetermined substance. For example, the image analysis apparatus 1 analyzes a sample image obtained by irradiating a biological tissue BT with light having an infrared bandwidth, and displays the sample image such that a predetermined substance in the tissue BT and a related particular part (for example, a part containing the predetermined substance or a part not containing the predetermined substance) are relatively emphasized. For example, the predetermined substance includes at least one of water, biomolecules such as lipid and protein, bloods, or lymph.

A tissue BT is, for example, a tissue of a human, or may be a tissue of a living organism (for example, an animal) other than a human. The tissue BT may be a tissue cut away from a living organism, or may be a tissue attached to a living organism. The tissue BT may be a tissue (biological tissue) of a living organism (living body), or may be a tissue of a dead organism (dead body). The tissue BT may be an object excised from a living organism. The tissue BT may include any organ of a living organism, may include a skin, and may include a viscus, which is on the inner side of the skin. The tissue BT may include either or both of secretions and excrement. The tissue BT may be a biological tissue added with a substance (for example, a fluorescent substance or a phosphorescent substance) that emits light by excitation when receiving light. The tissue BT may be fixed with use of a tissue fixative, such as formalin.

A spectrum (for example, an optical spectrum) of each part in the tissue BT exhibits a curve corresponding to optical properties (for example, absorbance, transmittance, and reflectance) of a composition (component) of the tissue BT. For example, the tissue BT in FIG. 1 includes a first part BTa and a second part BTb, and when the first part BTa and the second part BTb have different compositions, the spectrum of the first part BTa exhibits a curve different from that of the spectrum of the second part BTb. The image analysis apparatus 1 detects the difference in curve on the basis of non-linearity of the spectrum to determine a distribution of a predetermined substance. For example, the image analysis apparatus 1 specifies the difference (characteristics) of spectra of the first part BTa and the second part BTb on the basis of the non-linearity of the spectrum (first spectrum) of the first part BTa and the non-linearity of the spectrum (second spectrum) of the second part BTb to calculate a distribution of a predetermined substance.

The image analysis apparatus 1 performs an analysis by using sample data including data on a plurality of sample images. The sample image is an image obtained by detecting light having a predetermined wavelength band (for example, infrared light) among light radiated from the tissue BT irradiated with light having an infrared bandwidth. The light radiated from the tissue BT includes at least one of light reflected by the tissue BT when the tissue BT is irradiated with light, light transmitted through the tissue BT when the tissue BT is irradiated with light, or light (for example, fluorescence or phosphorescence) emitted from the tissue BT when the tissue BT is irradiated with light.

The sample image can be acquired by an imaging apparatus 2, such as a hyperspectral camera. For example, the imaging apparatus 2 including a hyperspectral camera includes a sensor capable of acquiring a plurality of pieces of spectrum data at one pixel in an image by single photographing. The spectrum of each part (for example, the first part BTa or the second part BTb) in the tissue BT is a distribution of light intensity with respect to the wavelength, and the light intensity is obtained from a pixel value in the sample image.

The image analysis apparatus 1 calculates an Nth-order derivative, where N is an integer of 2 or more, for at least a part (for example, a plurality of wavelengths or a particular wavelength band) of the spectrum obtained from sample data. For example, an Nth-order derivative (N is an integer of 2 or more) in a first wavelength band can be used as an index value indicating the shape of a curve of the spectrum in the first wavelength band. For example, when a part of the spectrum is approximated by a quadratic polynomial (when N=2), the second-order derivative of the polynomial has a value close to 0 in a part of the spectrum where the linearity is relatively strong. In a part of the spectrum where the non-linearity is relatively strong, the absolute value of the second-order derivative of the polynomial is large in accordance with the shape of the curve of the spectrum in the first wavelength band.

Figure 2:
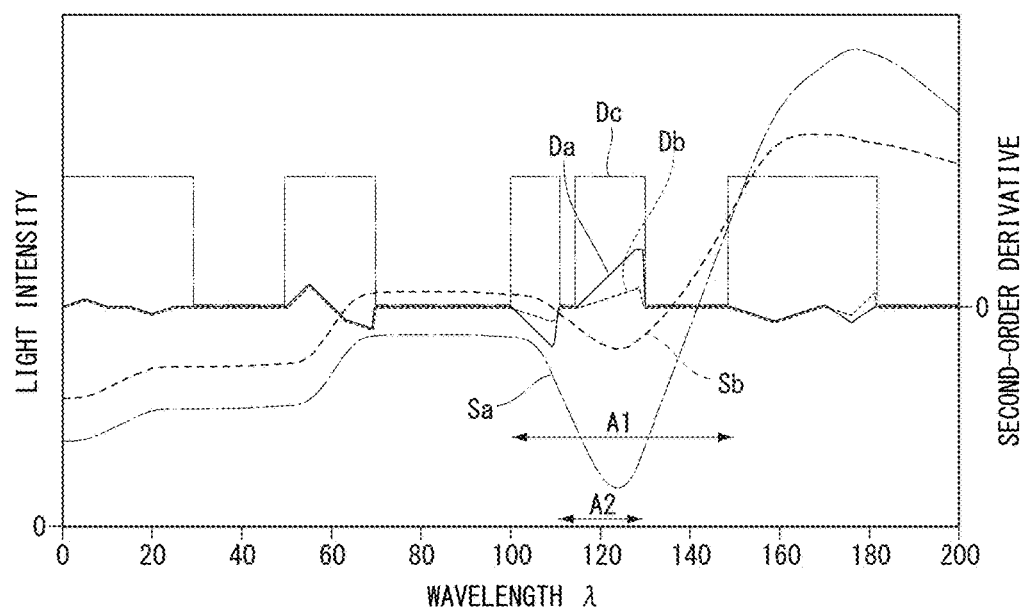
FIG. 2 is a graph schematically showing a spectrum and a distribution of second-order derivatives according to the present embodiment.

FIG. 2 is a graph schematically showing a spectrum obtained from sample data and a distribution of second-order derivatives. In FIG. 2, the horizontal axis represents the wavelength, the first vertical axis represents the light intensity, and the second vertical axis represents the second-order derivative. The unit of the horizontal axis, the unit of the first vertical axis, and the unit of the second vertical axis are each an arbitrary unit (hereinafter referred to as a.u.). In FIG. 2, a spectrum Sa is, for example, a spectrum of the first part BTa in FIG. 1, and a spectrum Sb is, for example, a spectrum of the second part BTb in FIG. 1. A distribution Da indicates a distribution of second-order derivatives of the spectrum Sa, and a distribution Db indicates a distribution of second-order derivatives of the spectrum Sb.

The spectrum Sa in FIG. 2 has a curve convex downward, for example, in a wavelength band A1 of wavelengths from 110 to 150. A wavelength band A2 of wavelengths from 110 to 130 is a wavelength band in which the spectrum Sa has a local minimum value, and the second-order derivative of the spectrum Sa is relatively large in the wavelength band A2. For example, when the second-order derivative of the spectrum Sa in the wavelength band A2 for each part of the tissue BT is calculated, the second-order derivative of the spectrum Sa is large for a part whose composition is similar to that of the first part BTa. For example, when the first part BTa contains a predetermined substance, the second-order derivative of the spectrum Sa is large for another part of the tissue BT that includes the predetermined substance.

For example, in FIG. 1, the content of a predetermined substance in the first part BTa of the tissue BT is a predetermined value or more, and the content of the predetermined substance in the second part BTb of the tissue BT is less than the predetermined value. For example, the image analysis apparatus 1 generates an image in which the first part BTa of the tissue BT is emphasized by gradation on the basis of an Nth-order derivative calculated by Nth-order differential processing of a spectrum obtained by irradiating the tissue BT with infrared light having a first wavelength band. For example, the image analysis apparatus 1 generates an image in which the first part BTa of the tissue BT is emphasized more than the second part BTb on the basis of a plurality of Nth-order derivatives (in this case, two Nth-order derivatives for each wavelength) calculated by Nth-order differential processing of a plurality of spectra (in this case, the spectrum Sa and the spectrum Sb) obtained by irradiating the first part BTa and the second part BTb with infrared light having a first wavelength band. For example, the image analysis apparatus 1 detects the first part BTa, and generates data on an image in which the detected first part BTa is emphasized more than the second part BTb. The image analysis apparatus 1 may detect the second part BTb, and generate data on an image in which the detected second part BTb is emphasized more than the first part BTa. In this manner, the image analysis apparatus 1 can use an Nth-order derivative (for example, a second-order derivative) obtained from a spectrum to detect a part of the tissue BT that satisfies the condition that the part contains a predetermined substance or a part of the tissue BT that satisfies the condition that the content of a predetermined substance is a threshold or more. For example, the image analysis apparatus 1 can use the second-order derivative as an index value to estimate the content of a predetermined substance in each part of the tissue BT.

In the wavelength band A2 in FIG. 2, the spectrum Sb has a curve convex downward, and the curve is gentler than that of the spectrum Sa. Thus, in the wavelength band A2, the second-order derivative of the spectrum Sb is smaller than the second-order derivative of the spectrum Sa. For example, in the wavelength band A2, the second-order derivative of the spectrum Sb is smaller than the second-order derivative of the spectrum Sa for a part of the tissue BT that has low similarity in composition to the first part BTa.

For example, the image analysis apparatus 1 can calculate an index value indicating similarity between one part and another part of the tissue BT, and generate data on an image indicating a distribution of the index value or data on an image in which one part and another part of the tissue BT are emphasized on the basis of a distribution of the index value. For example, when a user designates the first part BTa of the tissue BT on the sample image, the image analysis apparatus 1 can detect and extract a part of the tissue BT that satisfies the condition that the composition is similar to that of the first part BTa. For example, the image analysis apparatus 1 can use at least a part of the spectrum of the first part BTa as training data to calculate an index value indicating similarity to another part. For example, the image analysis apparatus 1 can compare a second-order derivative of the spectrum of the first part BTa in a predetermined wavelength band with a second-order derivative of the spectrum of another part in the predetermined wavelength band to calculate an index value indicating similarity between the first part BTa and another part.

In FIG. 2, a distribution Dc indicates a distribution of binary second-order derivatives. For example, the distribution Dc is a distribution that takes 0 when the second-order derivative in each wavelength calculated on the basis of the spectrum is less than a threshold and takes a predetermined value when the second-order derivative in each wavelength is a threshold or more. Binarizing the second-order derivative can detect, for example, a wavelength band having relatively high non-linearity in the spectrum. For example, binarizing the Nth-order derivative obtained from the spectrum can specify a wavelength band with non-linearity in the spectrum among a wavelength band with linearity (linear region) and a wavelength band with non-linearity (non-linear region).

While N is 2 in the above description, N may be 3, 4, 5, or 6 or more. Also when N is 3 or more, the shape of the spectrum can be evaluated for a part of the spectrum that has relatively strong non-linearity, for example.

Referring back to the description with reference to FIG. 1, each part in the image analysis apparatus 1 will be described. The image analysis apparatus 1 according to the present embodiment includes a distribution data generator 3, a differential calculator 4, an image data generator 5, a condition setter 6, a work memory 7, and a storage 8.

The work memory 7 includes, for example, a volatile memory, and is used as a temporary storage area for the processing performed by each part in the image analysis apparatus 1. The storage 8 includes, for example, a non-volatile memory or a large-scale storage area, and stores therein setting information for the processing performed by each part in the image analysis apparatus 1 and processing results of each part in the image analysis apparatus 1. The image analysis apparatus 1 is connected to a display device 9 such as a liquid crystal display, and outputs image data and text data indicating information stored in the storage 8 to the display device 9.

The condition setter 6 sets an analysis condition for the image analysis apparatus 1. Examples of the analysis condition include a wavelength band for which an Nth-order derivative is calculated. In the following description, the wavelength band for which the Nth-order derivative is calculated is referred to as analysis wavelength band as appropriate. For example, the analysis wavelength band is set to a wavelength band (for example, the wavelength band A1 or the wavelength band A2 in FIG. 2) including a non-linear part (non-linear region) of a distribution (spectrum) of light intensity with respect to the wavelength in the infrared bandwidth. A wavelength band including a non-linear part includes, for example, a wavelength in which the second-order derivative takes a value other than 0. For example, the analysis wavelength band is set to a wavelength band that includes an extreme value having a local maximum value or a local minimum value of a distribution of light intensity with respect to the wavelength in the infrared bandwidth.

The analysis wavelength band may be set to a wavelength band that does not include either of the local maximum value and the local minimum value of the distribution of light intensity with respect to the wavelength. For example, in the vicinity of a wavelength at which the distribution of light intensity takes an extreme value, the non-linearity of the distribution of light intensity is strong, and the second-order derivative for the wavelength takes a value corresponding to the non-linearity of the distribution of light intensity. For example, the wavelength band that includes a local maximum value or a local minimum value of the spectrum (for example, the above-described spectrum Sa or spectrum Sb) has strong non-linearity, and hence the Nth-order derivative of the spectrum in the wavelength band takes a value based on the non-linearity.

When the distribution of light intensity with respect to the wavelength is provided as discrete data, the local maximum value of the distribution may be, for example, a local maximum value obtained by converting the discrete data into a continuous function. The same is applied to the local minimum value. The continuous function is obtained by various kinds of approximation methods, such as the method of least squares. For example, the continuous function is selected from second-order differentiable function forms, and may be a polynomial function, a trigonometric function, or a spline function.

The analysis wavelength band is selected on the basis of a spectrum of a predetermined substance contained in the tissue BT. For example, the analysis wavelength band may be set to a wavelength band that includes a non-linear part of a spectrum of a predetermined substance. For example, the analysis wavelength band may be set to a wavelength band that includes an extreme value having a local maximum value or a local minimum value in an optical spectrum of a predetermined substance.

The analysis condition includes, for example, the condition for a region to be analyzed in a sample image. In the following description, the region to be analyzed is referred to as analysis region as appropriate. For example, the analysis region may be the entire region (all pixels) of the sample image, or may be the entire or part of a region (plurality of pixels) of the sample image where the tissue BT is shown. For example, when the analysis region includes a plurality of partial regions and each of the partial regions is analyzed, the condition for the analysis region includes the size of the partial region. The size of the partial region may be, for example, one pixel, a plurality of pixels, or nine pixels in three columns and three lines, and the number of pixels included in the partial region can be freely set. The plurality of partial regions may be regions obtained by dividing the analysis region without any overlap or may be regions in which one partial region partially overlaps with another partial region.

For example, default setting information for the analysis condition is stored in the storage 8. The image analysis apparatus 1 is connected to an input device 10, such as a mouse, a keyboard, a touch panel, or a trackball, and is capable of updating various kinds of setting information stored in the storage 8 to information input via the input device 10.

The distribution data generator 3 in FIG. 1 generates distribution data indicating a distribution of light intensity in the infrared bandwidth in the tissue BT on the basis of the captured sample image. The distribution data is data used to calculate the Nth-order derivative. The distribution data generator 3 extracts light intensity corresponding to each of M wavelengths of the analysis wavelength band, where M is an integer of N+1 or more, from the sample data. In the following description, the light intensity corresponding to the wavelength $\lambda$ is represented by $I(\lambda)$.

The distribution data generator 3 generates distribution data by using at least three wavelengths in the analysis wavelength band. For example, when N is 2 and M is 3, the distribution data generator 3 acquires $I(\lambda 1)$ from a pixel value of a first sample image in which light having the wavelength $\lambda 1$ is detected, acquires $I(\lambda 2)$ from a pixel value of a second sample image in which light having the wavelength $\lambda 2$ is detected, and acquires $I(\lambda 3)$ from a pixel value of a third sample image in which light having the wavelength λ3 is detected. The wavelength λ1, the wavelength λ2, and the wavelength λ3 are each selected from the analysis wavelength band.

For example, the distribution data generator 3 generates discrete data including N pairs of data, each of which is a pair of the wavelength and the light intensity paired with the wavelength, as distribution data. For example, the distribution data generator 3 generates distribution data including a pair (λ1,I(λ1)) of the wavelength λ1 and the light intensity I(λ1), a pair (λ2,I(λ2)) of the wavelength λ2 and the light intensity I(λ2), and a pair (λ3,I(λ3)) of the wavelength λ3 and the light intensity I(λ3).

The value of N is included in the analysis condition, for example. The value of N is set to 2 by default, and the value of N can be changed to an integer of 3 or more. The value of M is included in the analysis condition, for example. When N is 2, the value of M is set to 3 by default, and can be changed to an integer of 4 or more.

As shown in FIG. 2, for example, the distribution data generator 3 can generate distribution data including a wavelength band (for example, a first wavelength band) that includes three or more wavelengths. The distribution data generator 3 can generate distribution data for any desired wavelength band (for example, a first wavelength band) in a wavelength bandwidth corresponding to a plurality of sample images included in sample data. For example, when sample data is provided over a predetermined wavelength bandwidth, the distribution data generator 3 can generate distribution data for the entire wavelength bandwidth, and can generate distribution data for a part of the wavelength band. Distribution data setting information that defines the wavelength band of the distribution data generated by the distribution data generator 3 is included in the analysis condition and stored in the storage 8, for example.

For example, the distribution data generator 3 may generate distribution data only for a part of the wavelength band used to calculate the Nth-order derivative. The distribution data generator 3 may generate distribution data by using a wavelength band broader than a wavelength band that includes the wavelength band used to calculate the Nth-order derivative. For example, when distribution data over the entire wavelength bandwidth in which data on the distribution of light intensity exists is generated in advance and the wavelength band for distribution data to be output is designated, the distribution data generator 3 may extract and output distribution data for the designated wavelength band among the distribution data over the entire wavelength bandwidth.

In the present embodiment, the distribution data generator 3 generates distribution data for each of a plurality of partial regions included in the analysis region. The partial region includes, for example, a plurality of pixels in the sample image. For acquiring the light intensity I(λ1) corresponding to the wavelength λ1, for example, the distribution data generator acquires a pixel value of each of a plurality of pixels included in the partial region from sample data, and sets an average value of the acquired pixel values as the light intensity I(λ1) in the partial region. Similarly to the light intensity I(λ1), the distribution data generator sets an average value of pixel values of a plurality of pixels as the light intensity I(λ2) or the light intensity I(λ3). The distribution data generator 3 generates distribution data on the partial region on the basis of the light intensity I(λ1), the light intensity I(λ2), and the light intensity I(λ3) obtained from the average values of the pixel values of the plurality of pixels, and similarly generates distribution data for other partial regions. The number of pixels included in a partial region may be one or two or more.

The differential calculator 4 in FIG. 1 calculates, on the basis of the distribution data generated by the distribution data generator 3, an Nth-order derivative of the distribution of light intensity in the analysis wavelength band for each region (hereinafter referred to as unit region) in the sample image. For example, the unit region is set as the same region as the partial region (for example, one pixel or a plurality of pixels) used for the distribution data generator 3 to generate distribution data. For example, the distribution data generator 3 stores the generated distribution data in the storage 8, and the differential calculator 4 reads the distribution data from the storage 8 and calculates an Nth-order derivative in the unit region. The unit region may be different from the partial region used for the distribution data generator 3 to generate distribution data. For example, the unit region may extend over a plurality of continuous partial regions.

For example, when distribution data includes discrete data, the differential calculator 4 calculates an Nth-order derivative by a difference method. FIG. 3 shows an example of expressions used to calculate Nth-order derivatives. Expression (1) in FIG. 3 is an expression that represents a first-order derivative $d1(λn)$ for the wavelength λn by forward difference. Expression (2) in FIG. 3 is an expression that represents a second-order derivative $d2(λn)$ for the wavelength λn by forward difference.

The differential calculator 4 uses a pair of the wavelength λ1 and the light intensity I(λ1) and a pair of the wavelength λ2 and the light intensity I(λ2) in the distribution data to calculate $d1(λ1)$ in accordance with Expression (1). The differential calculator 4 uses a pair of the wavelength λ2 and the light intensity I(λ2) and a pair of the wavelength λ3 and the light intensity I(λ3) in the distribution data to calculate $d1(λ2)$ in accordance with Expression (1). The differential calculator 4 uses the calculated $d1(λ1)$ and $d1(λ2)$ to calculate the second-order derivative $d2(λ1)$ for λ1 in accordance with Expression (2).

While the calculation of Expression (1) and the calculation of Expression (2) are separately performed in the above description, the second-order derivative may be calculated by one expression by embedding Expression (1) in the right side $d1(λn+1)$ and $d1(λn)$ of Expression (2). The calculation of the first-order derivative may use either one of the central difference shown in Expression (3) and the backward difference shown in Expression (4). The calculation of the second-order derivative may use either one of the central difference shown in Expression (5) and the backward difference shown in Expression (6). The difference method used to calculate the second-order derivative may be the same as or different from the difference method used to calculate the first-order derivative. For example, the calculation of the first-order derivative and the calculation of the second-order derivative may each use the forward difference. The calculation of the first-order derivative may use the forward difference and the calculation of the second-order derivative may use the central difference.

As shown in FIG. 2, for example, the differential calculator 4 can calculate an Nth-order derivative for any desired wavelength within the range of the wavelength bandwidth in the distribution data generated by the distribution data generator 3. For example, the differential calculator 4 can calculate an Nth-order derivative for each of a plurality of wavelengths in a wavelength bandwidth in which the distribution data exists. For example, when the distribution data is generated over a predetermined wavelength bandwidth, the differential calculator 4 may calculate an Nth-order derivative only for one wavelength in the wavelength bandwidth, or may calculate an Nth-order derivative for each of two or more wavelengths in the wavelength bandwidth.

For example, the differential calculator 4 does not have to calculate Nth-order derivatives in wavelength bands other than the analysis wavelength band defined by the setting information. For example, before the analysis wavelength band is designated, the differential calculator 4 may calculate in advance Nth-order derivatives for respective wavelengths in the entire wavelength bandwidth in which the distribution data exists. In this case, when the analysis wavelength band is designated, the differential calculator 4 may extract and output an Nth-order derivative in the designated analysis wavelength band from among the Nth-order derivatives in the respective wavelengths in the entire wavelength bandwidth calculated in advance.

As described above, the differential calculator 4 calculates an Nth-order derivative for each region (for example, for each pixel or for each plurality of pixels) in the sample image, and stores the calculated Nth-order derivatives and positional information on the regions in the storage 8 in association with each other.

The image data generator 5 converts the Nth-order derivative into a gray-scale value to generate image data. For example, the image data generator 5 uses the Nth-order derivative to calculate a gray-scale value so that the Nth-order derivative and the gray-scale value have a substantially linear relation. For example, the image data generator 5 multiplies the absolute value of the Nth-order derivative by a conversion factor to calculate a gray-scale value. For example, the conversion factor may be set such that the value obtained by multiplying the absolute value of the Nth-order derivative by the conversion factor does not exceed an upper limit value of the pixel value. If the value obtained by multiplying the absolute value of the Nth-order derivative by the conversion factor exceeds the upper limit value of the pixel value, the image data generator 5 may convert the Nth-order derivative into the upper limit value of the pixel value.

A part of the analysis wavelength band where the Nth-order derivative is large is, for example, a part of the tissue BT that satisfies a predetermined condition (for example, the content of a predetermined substance is high). Accordingly, an image (hereinafter referred to as analysis image) indicated by image data generated by the image data generator 5 is, for example, an image in which a part of the tissue BT where the content of a predetermined substance is high is emphasized. For example, in the analysis image, a part of the tissue BT where the content of a predetermined substance is high is represented by a bright part whose gray-scale value is high, and a part of the tissue BT where the content of the predetermined substance is low is represented by a dark part whose gray-scale value is low.

The image data generator 5 may determine, as a gray-scale value, a value obtained by subtracting the value obtained by multiplying the absolute value of the Nth-order derivative by the conversion factor from the upper limit value (for example, 255 for 8 bits) of the pixel value in image data to be generated. In this case, in the analysis image, a part of the tissue BT where the content of a predetermined substance is high can be represented by a dark part, and a part of the tissue BT where the content of the predetermined substance is low can be represented by a bright part.

When the value obtained by multiplying the absolute value of the Nth-order derivative by the conversion factor is not an integer, the image data generator 5 may round the value, such as rounding-off, to calculate an integral gray-scale value. The image data generator 5 may calculate a gray-scale value so that the absolute value of the Nth-order derivative and the gray-scale value have a non-linear relation. The image data generator 5 may binarize the Nth-order derivative (into two levels) to generate image data. For example, the image data generator 5 may determine the pixel value of a pixel in the analysis image at which the Nth-order derivative in the analysis wavelength band is a threshold or more as the upper limit value (for example, 255 for 8 bits) and determine the pixel value of a pixel in the analysis image at which the Nth-order derivative in the analysis wavelength band is less than the threshold as the lower limit value (for example, 0 for 8 bits).

The image data generator 5 may use the calculated Nth-order derivative as an index value to generate data on an extracted image in which a part of the tissue BT that satisfies a predetermined condition (for example, the condition that the content of a predetermined substance is higher than a threshold) is extracted. For example, the image data generator 5 may generate data on an overlay image in which the extracted image is overlaid on a sample image. The image data generator 5 may generate data on an overlay image such that the extracted image and the sample image can be distinguished from each other. For example, the image data generator 5 may generate data on an overlay image in which the extracted image is represented by a color different from that of the sample image. For example, when the sample image is represented by the gray scale, the image data generator 5 may generate data on an overlay image such that the extracted image is represented by colors including a color other than the gray scale (for example, red, green, or blue). For example, the image data generator 5 may generate data on an overlay image in which a color image of the tissue BT and the extracted image are overlaid. The image data generator 5 may generate image data such that the extracted image blinks on the overlay image.

The image data generator 5 may generate data on an analysis image based on an Nth-order derivative for any desired wavelength in a wavelength band in which the Nth-order derivative calculated by the differential calculator 4 exists. For example, the image analysis apparatus 1 may use an Nth-order derivative for a wavelength designated by a user to generate data on an analysis image as needed, and display the analysis image on the display device 9. For example, the user can check the analysis image while switching the analysis wavelength band, and designate an analysis wavelength band with which a desired analysis image can be obtained.

Figures 4, 5:
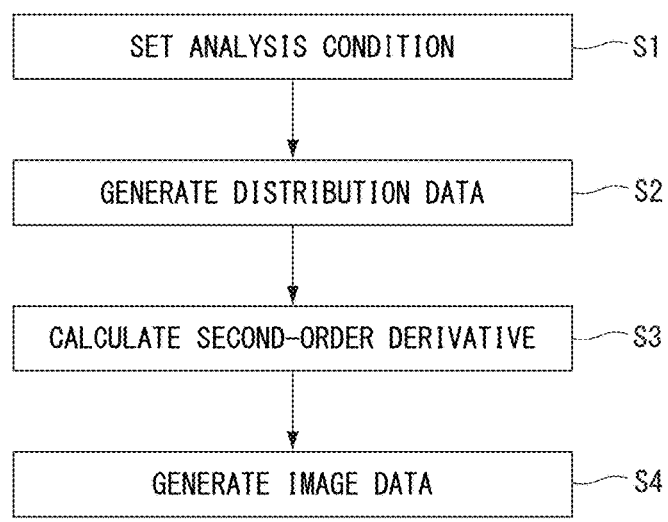
FIG. 4 is a flowchart showing an image analysis method according to the present embodiment.
FIG. 5 shows expressions for describing an Nth-order derivative calculation method in the present embodiment.

Next, an image analysis method according to the present embodiment will be described on the basis of the operation of the above-described image analysis apparatus 1. FIG. 4 is a flowchart showing the image analysis method according to the present embodiment. At Step S1, the image analysis apparatus 1 sets an analysis condition. For example, the image analysis apparatus 1 displays an image indicating a default analysis condition stored in the storage 8 on the display device 9. The image analysis apparatus 1 monitors an operation on the input device 10, and receives an input (input signal) such as a change of the analysis condition from a user. When the image analysis apparatus 1 detects that an input such as a change of the analysis condition is made on the input device 10, the image analysis apparatus 1 updates the analysis condition stored in the storage 8.

At next Step S2, the distribution data generator 3 generates distribution data. Prior to Step S2 or at Step S2, the image analysis apparatus 1 acquires sample data on a tissue BT. For example, the image analysis apparatus 1 is communicably connected to the imaging apparatus 2 that captures a sample image, and receives sample data on the tissue BT from the imaging apparatus 2. For example, the imaging apparatus 2 may repeatedly perform imaging processing, and the image analysis apparatus 1 may receive a part or whole of sample data for each imaging processing or each plurality of times of imaging processing. The sample data may be data based on a sample image captured in advance, or may be recorded in a recording medium or the like. The image analysis apparatus 1 may read sample data from the recording medium.

The distribution data generator 3 generates distribution data in accordance with, for example, the analysis condition stored in the storage 8. For example, the distribution data generator 3 reads setting information for an analysis region in the sample image and setting information for the distribution data from the storage 8. When a wavelength band defined by the distribution data setting information includes the wavelength $\lambda 1$, the wavelength $\lambda 2$, the wavelength $\lambda 3$, . . . , and the wavelength $\lambda n$, the distribution data generator 3 sequentially calculates light intensities in the analysis region at the respective wavelengths. For example, the distribution data generator 3 reads pixel values of a plurality of pixels included in a first partial region defined by the analysis region setting information from data on a first sample image that is detected with use of the wavelength $\lambda 1$. The distribution data generator 3 calculates an average value of the pixel values of the plurality of pixels, and determines the calculated average value as the light intensity $I(\lambda 1)$ in the first partial region at the wavelength $\lambda 1$. For the wavelength $\lambda 2$, the wavelength $\lambda 3$, . . . , and the wavelength $\lambda n$, the distribution data generator 3 similarly calculates the light intensity in the first partial region at the respective wavelengths. The distribution data generator 3 stores the wavelength and the calculated light intensity in the storage 8 in association with each other. Similarly to the first partial region, the distribution data generator 3 calculates the light intensity at each of the wavelength $\lambda 1$, the wavelength $\lambda 2$, the wavelength $\lambda 3$, . . . , and the wavelength $\lambda n$ in a second partial region defined by the analysis region setting information, and stores the wavelength and the calculated light intensity in the storage 8 in association with each other. In this manner, the distribution data generator 3 repeats the processing of generating distribution data for each partial region in the analysis region, thereby generating distribution data for the entire analysis region defined by the setting information.

At next Step S3, the differential calculator 4 calculates a second-order derivative. The differential calculator 4 generates distribution data in accordance with, for example, the analysis condition stored in the storage 8. For example, the differential calculator 4 reads the setting information that defines the analysis region, setting information that defines N (for example, 2 or 3 or more) in the analysis condition, and setting information that defines the analysis wavelength band from the storage 8.

The differential calculator 4 calculates an Nth-order derivative (in the case of FIG. 4, a second-order derivative) for each partial region in the analysis region. For example, the differential calculator 4 reads data on the first partial region among the distribution data generated by the distribution data generator 3 from the storage 8. The differential calculator 4 uses the light intensity in the wavelength band including the analysis wavelength band defined by the setting information among the distribution data to calculate the second-order derivative in accordance with, for example, Expression (1) and Expression (2) in FIG. 3. For example, when the analysis wavelength band defined by the setting information includes the wavelength $\lambda 1$, the wavelength $\lambda 2$, the wavelength $\lambda 3$, . . . , and the wavelength $\lambda n$, the differential calculator 4 sequentially calculates second-order derivatives at the respective wavelengths. For the first partial region, for example, the differential calculator 4 stores each wavelength and the calculated second-order derivative in the storage 8 in association with each other.

For the second partial region in the analysis region, the differential calculator 4 similarly calculates an Nth-order derivative (in the case of FIG. 4, a second-order derivative) at each wavelength in the analysis wavelength band, and stores each wavelength and the calculated second-order derivative in the storage 8 in association with each other. For example, the differential calculator 4 repeats the processing of calculating the second-order derivative at each wavelength in the analysis wavelength band for each partial region, thereby calculating the second-order derivative for each of the plurality of partial regions included in the analysis region defined by the setting information.

At next Step S4, the image data generator 5 generates analysis image data on the basis of the Nth-order derivative (in the case of FIG. 4, the second-order derivative) calculated by the differential calculator 4. For example, the image analysis apparatus 1 stores the analysis image data generated by the image data generator 5 in the storage 8, and outputs the analysis image data to the display device 9 in response to an instruction from the user.

In the present embodiment, the distribution data indicating the distribution of light intensity in the infrared bandwidth in the tissue BT is generated, the Nth-order derivative of the distribution of light intensity is calculated for each region in the sample image on the basis of the distribution data, and the Nth-order derivative is converted into a grayscale value to generate image data. Consequently, a composition of the biological tissue BT can be accurately analyzed. The image analysis apparatus 1 in the present embodiment can accurately obtain information on the biological tissue BT.

Second Embodiment

Next, a second embodiment will be described. In the present embodiment, the distribution data generator 3 calculates a continuous function indicating a distribution of light intensity in a wavelength band including an analysis wavelength band. The differential calculator 4 uses the continuous function to calculate an Nth-order derivative.

For example, the distribution data generator 3 calculates a continuous function indicating a distribution of light intensity in a wavelength band including an analysis wavelength band, and generates parameters indicating the continuous function as distribution data. For example, when a pair of the wavelength $\lambda 1$ and the light intensity $I(\lambda 1)$, a pair of the wavelength $\lambda 2$ and the light intensity $I(\lambda 2)$, and a pair of the wavelength $\lambda 3$ and the light intensity $I(\lambda 3)$ are used, a unique quadratic function for the light intensity $I(\lambda)$ where $\lambda$ is variable is determined. For example, the distribution data generator 3 generates a pair of coefficients of respective terms of the quadratic function as distribution data. The distribution data generator 3 may generate distribution data that includes a coefficient of a quadratic term among the coefficients of the quadratic function.

The distribution data generator 3 may use N+1 or more pairs of the wavelength and the light intensity to calculate an Nth-order polynomial function as the above-described continuous function. For example, the distribution data generator 3 may use four pairs of the wavelength and the light intensity to calculate a third-order polynomial function as the continuous function. In this case, the distribution data generator 3 may generate a pair of coefficients of at least second- or higher-order terms of the third-order polynomial function as distribution data.

The distribution data generator 3 may calculate an approximate expression of the distribution of light intensity in the wavelength band including the analysis wavelength band as the above-described continuous function. For example, the distribution data generator 3 may use four pairs of the wavelength and the light intensity to calculate an approximate expression of a quadratic function by various kinds of approximation methods, such as the method of least squares, and generate distribution data including a coefficient of at least the second-order term among coefficients of the quadratic function. For example, the use of the approximate expression can reduce the influence of noise. Third- or higher-order approximation expressions may be used. The number of pairs of the wavelength and the light intensity used to calculate an approximate expression of an Nth-order function can be set to any desired number of N+1 or more.

For example, the differential calculator 4 uses the coefficient of the continuous function calculated by the distribution data generator 3 to calculate an Nth-order derivative. FIG. 5 shows expressions for describing an example of a method of calculating an Nth-order derivative by the differential calculator 4 according to the present embodiment. The Nth-order polynomial is expressed by Expression (7) in FIG. 5. In Expression (7), $C_i$ is a coefficient of the i-order term, where i is an integer of 0 or more and N or less. $C_i$ is data included in the distribution data generated by the distribution data generator 3. The second-order derivative for the wavelength $\lambda n$ is expressed by Expression (8) in FIG. 5. The differential calculator 4 uses $C_i$ included in the distribution data to calculate the second-order derivative in accordance with Expression (8), for example.

In this case, for example, when the quadratic function that approximates the distribution of light intensity in the analysis wavelength band is subjected to second-order differentiation, the coefficient of the second-order term is left. Thus, even when the analysis wavelength band is set to a wavelength band that does not include either of the local maximum value and the local minimum value, the same result as in the case where the second-order derivative is determined in a wavelength band including the local maximum value or the local minimum value can be obtained.

Third Embodiment

Figure 6:
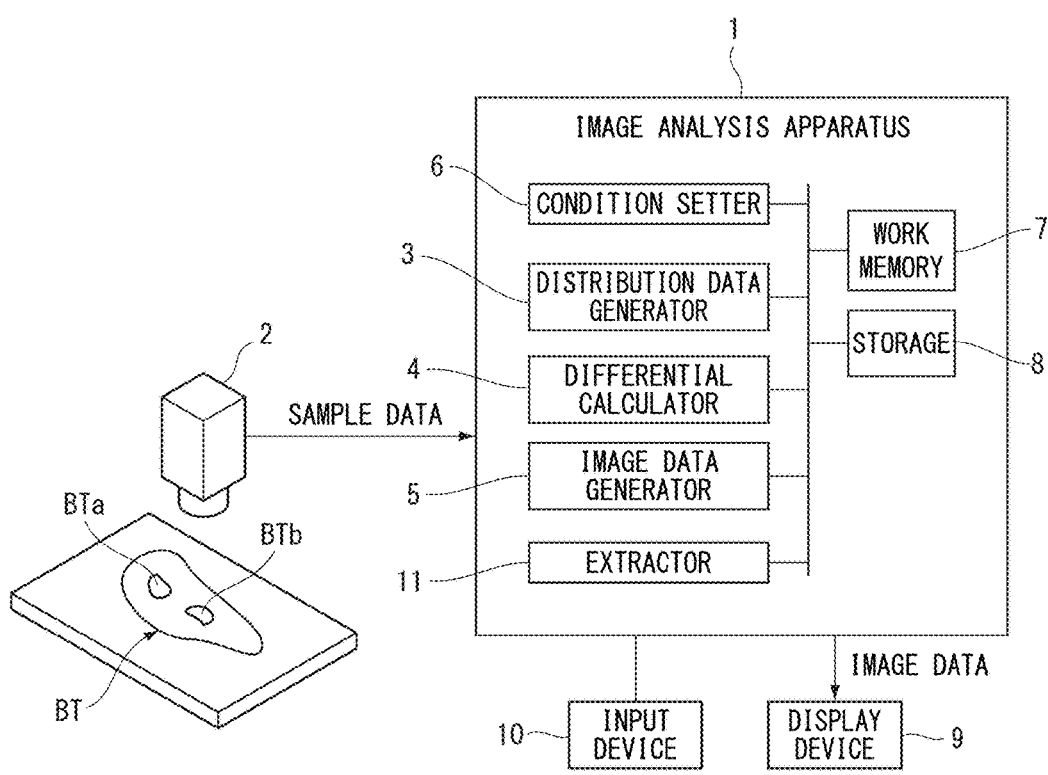
FIG. 6 is a diagram showing an image analysis apparatus according to the present embodiment.

Next, a third embodiment will be described. FIG. 6 is a diagram showing an image analysis apparatus 1 according to the present embodiment. The image analysis apparatus 1 includes an extractor 11 in addition to the above-described configuration. In the present embodiment, the differential calculator 4 calculates an Nth-order derivative for each of a plurality of wavelengths, and the extractor 11 uses the calculation results of the differential calculator 4 to extract a wavelength band (for example, a first wavelength band) in which the absolute value of the Nth-order derivative is a threshold or more. For example, extraction setting information that defines the threshold is included in the analysis condition and stored in the storage 8.

For example, the extractor 11 reads the extraction setting information from the storage 8. When the wavelength $\lambda 1$, the wavelength $\lambda 2$, the wavelength $\lambda 3$, . . . , and the wavelength $\lambda n$ are included in a wavelength band for which an Nth-order derivative is calculated by the differential calculator 4, for example, the extractor 11 reads an Nth-order derivative at the wavelength $\lambda 1$, and compares the Nth-order derivative with a threshold. When the Nth-order derivative at the wavelength $\lambda 1$ is a threshold or more, the extractor 11 stores the wavelength $\lambda 1$ in the work memory 7, for example. For each of the wavelength $\lambda 2$, the wavelength $\lambda 3$, . . . , and the wavelength $\lambda n$, the extractor 11 sequentially reads Nth-order derivatives, and when the Nth-order derivative is a threshold or more, stores the wavelength in the work memory 7. After the comparison processing is finished for the wavelength $\lambda n$, the extractor 11 stores the wavelengths stored in the work memory 7 in the storage 8 as a set of extraction data.

For example, the image analysis apparatus 1 may replace the Nth-order derivative at each wavelength extracted by the extractor 11 with a first predetermined value, and replace an Nth-order derivative at a wavelength that is not extracted by the extractor 11 among the wavelength $\lambda 1$, the wavelength $\lambda 2$, the wavelength $\lambda 3$, and the wavelength $\lambda n$ with a second predetermined value. In this manner, for example, as indicated by the distribution Dc shown in FIG. 2, data in which the Nth-order derivative is binarized to the first predetermined value or the second predetermined value can be obtained.

In each of the above-described embodiments, the image analysis apparatus 1 may perform image analysis by using a first-order derivative in addition to the above-described Nth-order derivative. For example, the image analysis apparatus 1 may include a detector that detects the wavelength at which the distribution of light intensity has an extreme value by using the Nth-order derivative and the first-order derivative. For example, the image analysis apparatus 1 may use information on the wavelength detected by the detector to set the analysis wavelength band. For example, the image analysis apparatus 1 may display the information on the wavelength detected by the detector on the display device 9 as a candidate of the analysis wavelength band. In each of the above-described embodiments, the distribution data generator 3 in the image analysis apparatus 1 may output, before generating the above-described distribution data and before calculating the above-described Nth-order derivative, as preprocessing, data obtained by L-order differentiation (L is an integer of 1 or more including 0) of the spectrum as the distribution data in order to specify an extreme value of the spectrum. As the preprocessing, the distribution data generator 3 may smooth the spectrum by the method of moving averages. In this manner, the distribution data generator 3 may perform the above-described preprocessing to obtain an approximated curve of the spectrum before generating the distribution data. The preprocessing enables the image analysis apparatus 1 to generate an image in which the influence of noise included in the spectrum is reduced and analyze a sample image with high accuracy.

EXAMPLE

Figure 7:
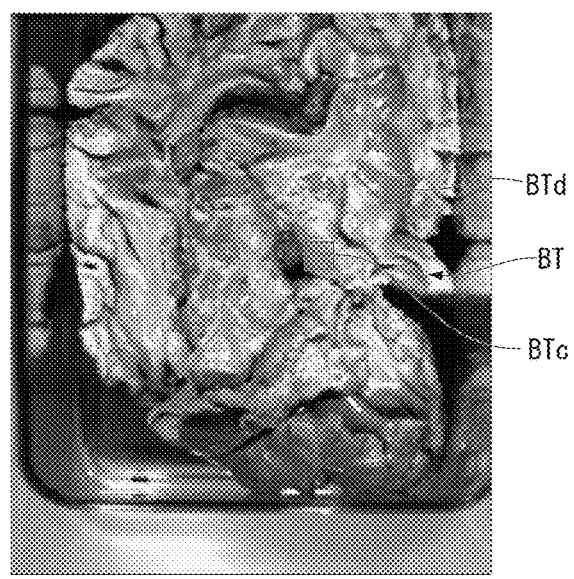
FIG. 7 is a diagram showing an example of a sample image according to Example.

Next, Example will be described. FIG. 7 is a diagram showing an example of a sample image according to Example. A tissue BT shown in the sample image in FIG. 7 includes mesenteries. A part BTc in the tissue BT is a part in which the proportion of water is larger than that in a part BTd. The part BTd is a part in which the proportion of lipid is larger than that in the part BTc. The part BTc is a part including a lymph node, for example, and the part BTd is a part including a skin and fats.

Figure 8:
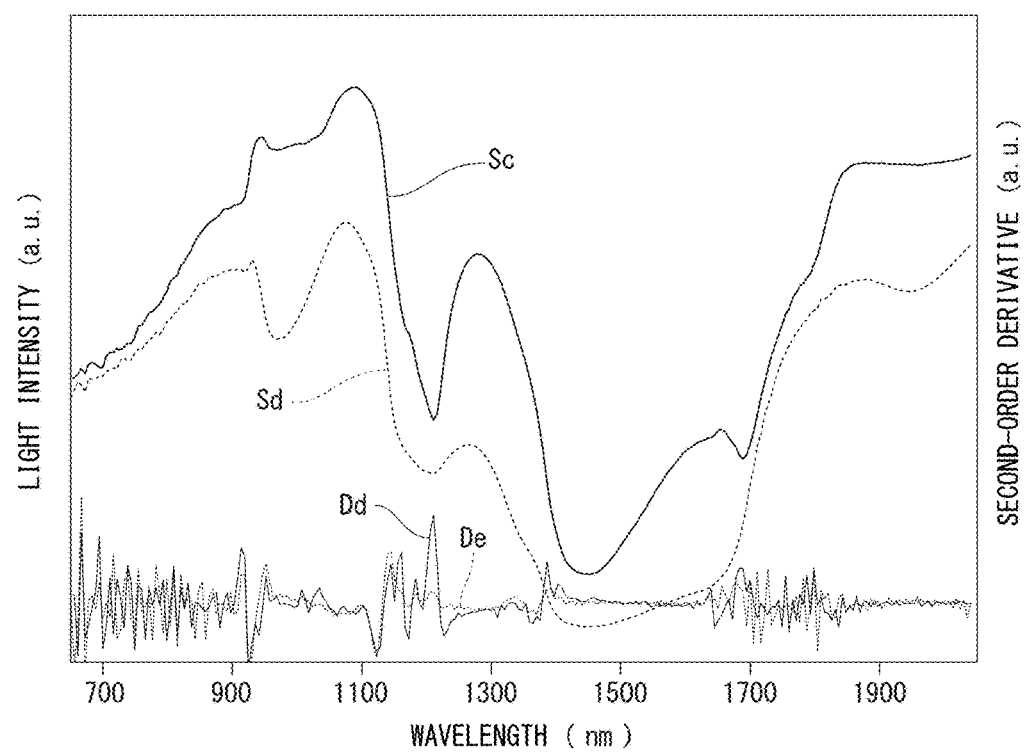
FIG. 8 is a diagram showing a spectrum and a distribution of second-order derivatives according to Example.

FIG. 8 is a diagram showing a spectrum and a distribution of second-order derivatives according to Example. In FIG. 8, a spectrum Sc indicates a spectrum of the part BTc, and a spectrum Sd indicates a spectrum of the part BTd. A distribution Dd indicates a distribution of second-order derivatives of the spectrum Sc, and a distribution De indicates a distribution of second-order derivatives of the spectrum Sd. In FIG. 8, the horizontal axis is the wavelength $\lambda$ (nm), the first vertical axis is the light intensity I, and the second vertical axis is the second-order derivative. The units of the light intensity I and the second-order derivative are arbitrary units (a.u.).

The spectrum Sc has a local maximum value or a local minimum value in each of a wavelength band of wavelengths from 900 nm or more to 1100 nm or less, a wavelength band from 1100 nm or more to 1300 nm or less, a wavelength band from 1500 nm or more to 1700 nm or less, and a wavelength band from 1600 nm or more to 1800 nm or less. The spectrum Sc has a local minimum value in a wavelength band from 1300 nm or more to 1500 nm or less. In the distribution Dd of second-order derivatives, the absolute value of the second-order derivative is large in the vicinity of a wavelength at which the spectrum Sc takes a local maximum value and in the vicinity of a wavelength at which the spectrum Sc takes a local minimum value. The distribution Dd of second-order derivatives shows that the second-order derivative has a relatively large value in a wavelength band including a wavelength at which the spectrum Sc takes a local maximum value or a local minimum value.

The spectrum Sd has a local maximum value or a local minimum value in each of a wavelength band of wavelengths from 900 nm or more to 1100 nm or less, a wavelength band from 1100 nm or more to 1300 nm or less, and a wavelength band from 1800 nm or more to 2000 nm or less. The spectrum Sd has a local minimum value in a wavelength band from 1300 nm or more to 1500 nm or less. In the distribution De of second-order derivatives, the absolute value of the second-order derivative is large in the vicinity of a wavelength at which the spectrum Sd takes a local maximum value and in the vicinity of a wavelength at which the spectrum Sd takes a local minimum value. The distribution De of second-order derivatives shows that the second-order derivative has a relatively large value in a wavelength band including a wavelength at which the spectrum Sd takes a local maximum value or a local minimum value.

In FIG. 8 in Example, a wavelength band from 900 nm or more to 1100 nm or less, a wavelength band from 1100 nm or more to 1300 nm or less, a wavelength band from 1150 nm or more to 1250 nm or less, a wavelength band from 1300 nm or more to 1500 nm or less, a wavelength band from 1350 nm or more to 1450 nm or less, a wavelength band from 1500 nm or more to 1700 nm or less, a wavelength band from 1600 nm or more to 1800 nm or less, and a wavelength band from 1800 nm or more to 2000 nm or less each include a wavelength at which the difference between the second-order derivative of the spectrum Sc and the second-order derivative of the spectrum Sd is noticeable. In Example, for example, a wavelength selected from such a wavelength band is set as an analysis wavelength band. In Example, for example, a wavelength at which the second-order derivative of the spectrum Sd of the part BTd having a large proportion of lipid is larger than the second-order derivative of the spectrum Sc of the part BTc having a large proportion of water is set as an analysis wavelength band. For example, the analysis wavelength band is set to a wavelength band including at least one of a wavelength band from 900 nm or more to 1100 nm or less, a wavelength band from 1100 nm or more to 1300 nm or less, a wavelength band from 1150 nm or more to 1250 nm or less, a wavelength band from 1300 nm or more to 1500 nm or less, a wavelength band from 1350 nm or more to 1450 nm or less, a wavelength band from 1500 nm or more to 1700 nm or less, a wavelength band from 1600 nm or more to 1800 nm or less, a wavelength band from 1800 nm or more to 2000 nm or less, a wavelength band from 1000 nm or more to 1500 nm or less, or a wavelength band from 900 nm or more to 1700 nm or less.

Figure 9:
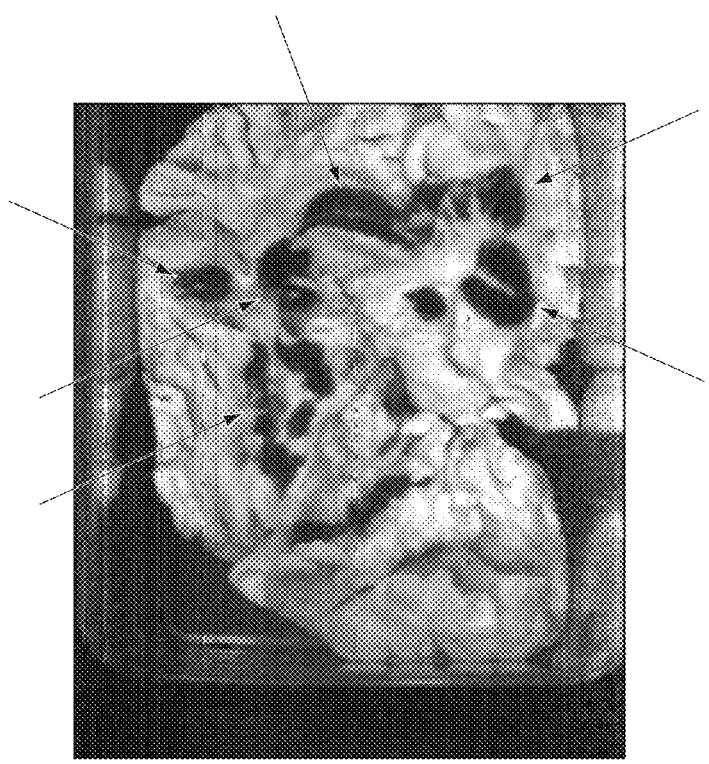
FIG. 9 is a diagram showing an example of an analysis image according to Example.

FIG. 9 is a diagram showing an example of an analysis image according to Example. As shown in FIG. 9, parts (indicated by arrows in the figure) corresponding to lymph nodes are represented by dark parts whose gray-scale values are low. Parts corresponding to the skin and fats are represented by bright parts whose gray-scale values are high. In this manner, it was confirmed that an image in which parts of the tissue BT that satisfy a predetermined condition were emphasized was able to be obtained.

Figure 10:
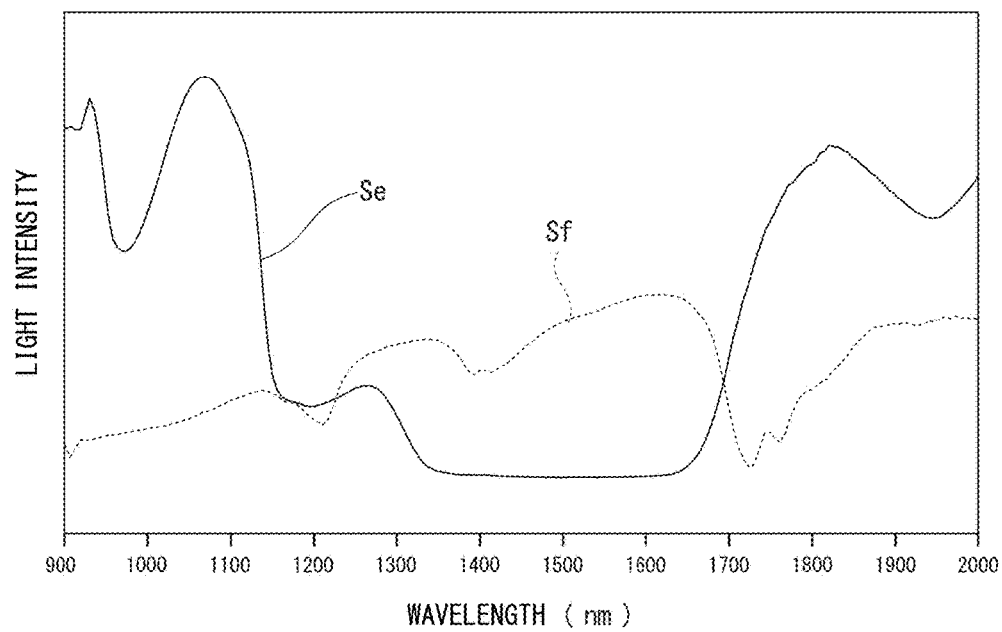
FIG. 10 is a graph showing an example of an optical spectrum of a predetermined substance according to the present embodiment.

The analysis wavelength band may be set on the basis of a spectrum (for example, an optical spectrum) of a predetermined substance contained in the tissue BT. FIG. 10 is a graph showing an example of a spectrum (for example, an optical spectrum) of a predetermined substance according to the present embodiment. In FIG. 10, a spectrum Se is a spectrum of water (for example, 10 mm in thickness), and a spectrum Sf is a spectrum of lipid. In FIG. 10, the horizontal axis is the wavelength $\lambda$ (nm), and the vertical axis is the light intensity I (a.u.).

The spectrum Se of water has a local maximum value or a local minimum value in each of a wavelength band from 900 nm or more to 1100 nm or less and a wavelength band from 1100 nm or more to 1300 nm or less. The spectrum Se of water has a local maximum value in a wavelength band from 1700 nm or more to 1900 nm or less. The spectrum Se of water has a local minimum value in a wavelength band from 1900 nm or more to 2000 nm or less. The spectrum Sf of lipid has a local maximum value or a local minimum value in each of a wavelength band from 1100 nm or more to 1300 nm or less and a wavelength band from 1300 nm or more to 1500 nm or less. The spectrum Sf of lipid has a local maximum value in a wavelength band from 1500 nm or more to 1700 nm or less. Setting an analysis wavelength band to a wavelength band in which the spectrum has either or both of the local maximum value and the local minimum value makes it easy to detect the distribution of a predetermined substance in the tissue BT. Setting a wavelength band in which the spectrum of one of lipid and water has strong non-linearity and the spectrum of the other has strong linearity as an analysis wavelength band makes it easy to distinguish a part of the tissue BT having a large proportion of lipid from a part of the tissue BT having a large proportion of water.

Thus, for example, when the predetermined substance includes lipid or water, the analysis wavelength band may be set to a wavelength band from 900 nm or more to 1700 nm or less. The analysis wavelength band may be set to a wavelength band including at least one of a wavelength band from 900 nm or more to 1100 nm or less, a wavelength band from 1100 nm or more to 1300 nm or less, a wavelength band from 1300 nm or more to 1500 nm or less, a wavelength band from 1500 nm or more to 1700 nm or less, or a wavelength band from 1900 nm or more to 2000 nm or less.

Figure 11:
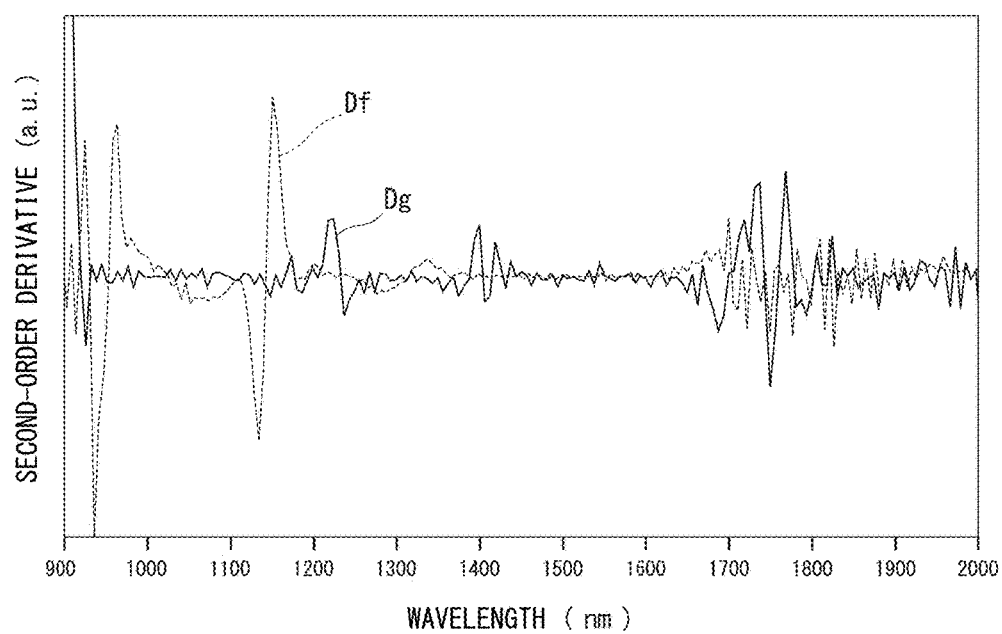
FIG. 11 is a diagram showing an example of a distribution of second-order derivatives corresponding to the optical spectrum according to the present embodiment.

FIG. 11 is a diagram showing an example of a distribution of second-order derivatives corresponding to a spectrum according to the present embodiment. In FIG. 11, a distribution Df indicates a distribution of second-order derivatives corresponding to a spectrum (for example, an optical spectrum) of water, and a distribution Dg indicates a distribution of second-order derivatives corresponding to a spectrum (for example, an optical spectrum) of lipid. In FIG. 11, the horizontal axis is the wavelength λ (nm), and the vertical axis is the second-order derivative (a.u.).

FIG. 11 shows that the distribution Df of second-order derivatives for water has a wavelength at which the second-order derivative is noticeably large in each of a wavelength band from 900 nm or more to 1000 nm or less, a wavelength band from 1000 nm or more to 1100 nm or less, a wavelength band from 1100 nm or more to 1200 nm or less, a wavelength band from 1100 nm or more to 1300 nm or less, a wavelength band from 1300 nm or more to 1400 nm or less, and a wavelength band from 1650 nm or more to 1900 nm or less. The distribution Dg for lipid has a wavelength at which the second-order derivative is noticeably large in each of a wavelength band from 1100 nm or more to 1200 nm or less, a wavelength band from 1150 nm or more to 1300 nm or less, a wavelength band from 1350 nm or more to 1450 nm or less, and a wavelength band from 1650 nm or more to 1850 nm or less. Thus, the analysis wavelength band may be set to a wavelength band including at least one of a wavelength band from 900 nm or more to 1000 nm or less, a wavelength band from 1000 nm or more to 1100 nm or less, a wavelength band from 1100 nm or more to 1200 nm or less, a wavelength band from 1100 nm or more to 1300 nm or less, a wavelength band from 1150 nm or more to 1300 nm or less, a wavelength band from 1300 nm or more to 1400 nm or less, a wavelength band from 1350 nm or more to 1450 nm or less, a wavelength band from 1650 nm or more to 1850 nm or less, or a wavelength band from 1650 nm or more to 1900 nm or less.

The number of kinds of predetermined substances may be one or two or more. For example, a first analysis wavelength band may be selected on the basis of a spectrum of a first predetermined substance, and a second analysis wavelength band different from the first analysis wavelength band may be selected on the basis of a spectrum of a second predetermined substance. For example, the image analysis apparatus 1 may use an Nth-order derivative in the first analysis wavelength band to detect a distribution of the first predetermined substance in the tissue BT, and may use an Nth-order derivative in the second analysis wavelength band to detect a distribution of the second predetermined substance in the tissue BT. For example, the first predetermined substance may include water, and the second predetermined substance may include lipid.

For example, the image analysis apparatus 1 includes a computer that executes various kinds of processing in accordance with an image analysis program read from a storage device (not shown). The image analysis program causes the computer to execute: generating, on the basis of a sample image obtained by irradiating a biological tissue with light having an infrared bandwidth, distribution data indicating a distribution of light intensity in the infrared bandwidth in the tissue; calculating, on the basis of the distribution data, an Nth-order derivative of a distribution of light intensity in a first wavelength band of the infrared bandwidth, where N is an integer of 2 or more, for each region in the sample image; and converting the Nth-order derivative into a gray-scale value to generate image data. The image analysis program may be recorded in a computer-readable recording medium, or may be provided via a communication line.

Figure 12:
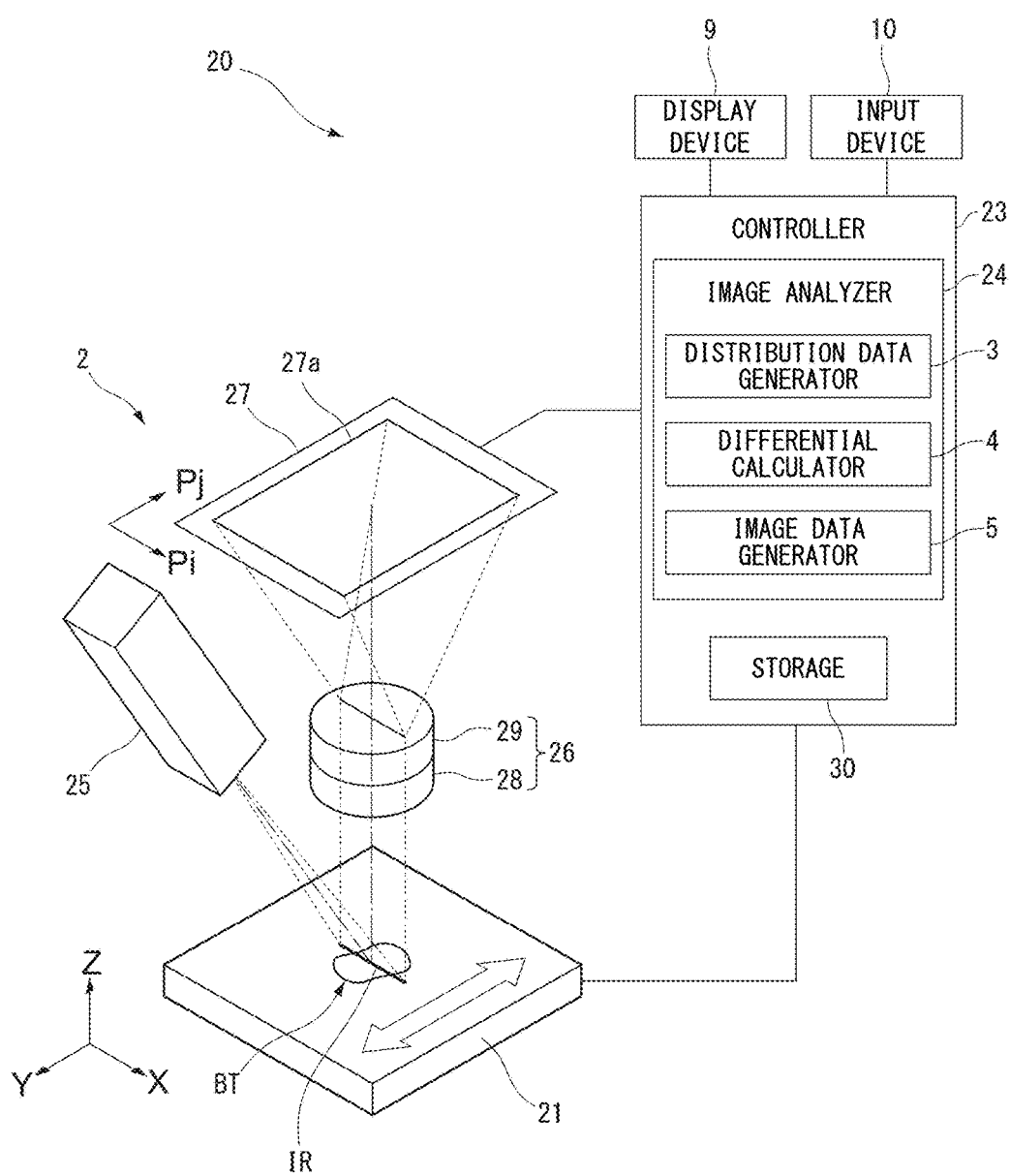
FIG. 12 is a diagram showing an imaging system according to the present embodiment.

Next, an imaging system according to the present embodiment will be described. FIG. 12 is a diagram showing an imaging system 20 according to the present embodiment. On the basis of a sample image in which a biological tissue BT is imaged with use of infrared light in the above-described analysis wavelength band, the imaging system 20 optically detects a part of the tissue BT in which the composition satisfies a predetermined condition.

The imaging system 20 is used for pathological anatomy, pathological diagnosis, and biopsy for a tissue BT, a biological operation (for example, a surgical operation), and other purposes. The imaging system 20 can be applied to medical applications, test applications, and examination applications, including procedures (invasive procedures) involving an incision of a tissue BT, such as a general operation, and various kinds of tests (non-invasive tests) involving no incision of a tissue BT.

The imaging system 20 includes a stage device 21, an imaging apparatus (imaging unit) 2, a controller 23, an input device 10, and a display device (display) 9. The imaging system 20 operates as follows, for example. A tissue BT can be disposed on the top surface of the stage device 21. The imaging apparatus 2 captures an image of a biological tissue BT disposed on the stage device 21. The input device 10 can receive an input from an operator (user), for example. The controller 23 controls each part in the imaging system 20 on the basis of instructions and settings input to the input device 10 from the user, for example. An image analyzer 24 (image analysis apparatus) is embedded in the controller 23. The image analyzer 24 generates image data indicating a spatial distribution of parts in the tissue BT that satisfy a predetermined condition on the basis of a sample image in which the tissue BT is imaged. For example, the image analyzer 24 generates image data indicating a distribution of substances in the tissue BT. The controller 23 displays various kinds of information on the display device 9. For example, the controller 23 uses the image data generated by the image analyzer 24 to display an image indicating a distribution of substances in the tissue BT on the display device 9. Each part in the imaging system 20, a method of generating image data, and the like will be described below.

The imaging apparatus 2 can detect light intensity of light for each wavelength, which is radiated from at least a part of the tissue BT when the tissue BT is illuminated with light output from a light source 25. For example, the imaging apparatus 2 can acquire a hyperspectral image as exemplified by a hyperspectral camera. The imaging apparatus 2 can acquire spectrum data on light radiated from a part (a region to be captured) of the tissue BT by single imaging. The imaging apparatus 2 can capture images of a plurality of regions on the tissue BT, thereby acquiring a spatial distribution of light intensity of the light radiated from the tissue ST. The imaging apparatus 2 can capture a plurality of sample images while moving regions to be captured on the tissue BT, thereby acquiring a spatial distribution of light intensity in any desired wavelength of the light radiated from the tissue BT and acquiring a distribution of light intensity with respect to the wavelength of light radiated from any desired position on the tissue BT. The imaging apparatus 2 includes the light source 25, an imaging optical system 26, and a light detector 27.

The light source 25 includes, for example, a halogen lamp or an infrared LED (infrared light emitting diode). The light source 25 outputs light in a wavelength band used for image analysis by the image analyzer 24. The wavelength band used for image analysis is, for example, at least a part of a wavelength bandwidth from 900 nm or more to 1700 nm or less or a wavelength bandwidth from 900 nm or more to 2000 nm or less. Accordingly, the light source 25 in the imaging apparatus 2 can radiate light having a wavelength bandwidth including at least a part of a wavelength bandwidth from 900 nm or more to 1700 nm or less or a wavelength bandwidth from 900 nm or more to 2000 nm or less.

The light source 25 illuminates a lighting region IR on the stage device 21 with infrared light. The lighting region IR is set as a linear shape elongated in one direction. In the present embodiment, the light source 25 outputs infrared light having a spot shape elongated in one direction.

Referring to an XYZ orthogonal coordinate system shown in FIG. 12, the positional relation among elements and the like will be described below. In the XYZ orthogonal coordinate system, the longitudinal direction of the lighting region IR is referred to as X-axis direction, and the direction orthogonal to the X-axis direction on the stage device 21 is referred to as Y-axis direction. The direction orthogonal to each of the X-axis direction and the Y-axis direction is referred to as Z-axis direction. The X-axis direction and the Y-axis direction are set to the horizontal direction, for example, and the Z-axis direction is set to the vertical direction, for example.

The imaging optical system 26 guides light radiated from the lighting region IR (tissue BT) on the stage device 21 to the light detector 27. The imaging optical system 26 includes a lens 28 and a spectrometer 29. The lens 28 condenses the light radiated from the tissue BT onto the light detector 27. The spectrometer 29 includes, for example, at least one of a prism, a diffraction grating, or a slit, and disperses the light radiated from the tissue BT into components in a plurality of wavelength bands. The spectrometer 29 disperses light radiated from each point on the tissue BT into spectral light having a spot shape elongated in the Y-axis direction. For example, the spectrometer 29 disperses short-wavelength components in the spectral light to one side in the Y-axis direction, and disperses long-wavelength components in the spectral light to the other side in the Y-axis direction.

The light detector 27 includes a two-dimensional image sensor, such as a CMOS sensor or a CCD sensor. The light detector 27 has a light receiving surface 27a on which photoelectric conversion elements such as photodiodes are arranged. On the light receiving surface 27a, a region where one photodiode is disposed corresponds to one pixel. In the following description, on the light receiving surface 27a, the direction corresponding to the longitudinal direction of the lighting region IR is referred to as Pi direction, and the direction orthogonal to the Pi direction is referred to as Pj direction. The Pi direction is a vertical scanning direction, for example, and the Pj direction is a horizontal scanning direction, for example. Pixels in the light detector 27 are arranged in each of the Pi direction and the Pj direction. The light detector 27 operates as at least a part of the above-described hyperspectral camera.

Attention is now focused on a plurality of pixels arranged in the Pj direction (horizontal scanning line). The spectrometer 29 disperses light radiated from each point on the tissue BT into spectral light that distributes in the direction orthogonal to the longitudinal direction of the lighting region IR. Accordingly, a short-wavelength component in the spectral light enters a pixel disposed on one end side in the horizontal scanning line, and a long-wavelength component in the spectral light enters a pixel disposed on the other end side in the horizontal scanning line. In this manner, the light detector 27 can detect light radiated from a part on the tissue BT separately for each wavelength band by using the plurality of pixels arranged on the horizontal scanning line. For example, the light source 25 outputs infrared light over a broad wavelength bandwidth, and the plurality of pixels in the light detector 27 each detect light having a wavelength band narrower than that of the infrared light output from the light source 25.

For example, the wavelength of light entering a pixel disposed on one end in the horizontal scanning line is represented by $\lambda 4$, and the wavelength of light entering a pixel on the other end in the horizontal scanning line is represented by $\lambda 5$. When the number of pixels arranged on the horizontal scanning line is K (K is an integer of 1 or more), the light detector 27 can detect light having a wavelength bandwidth from the wavelength $\lambda 4$ to the wavelength $\lambda 5$ separately for each of K wavelength bands. In the following, the width of each wavelength band for detecting the light intensities separately for a plurality of wavelength bands is referred to as detection width as appropriate. The detection width depends on $\lambda 4$, $\lambda 5$, and K. For example, when the number of pixels in the horizontal scanning direction is 1280, the detection width can be set to about several nm (for example, 1 nm or more and less than 10 nm).

The detection width can be freely set. For example, the detection width can be narrowed (for example, to less than 1 nm) as a smaller difference between $\lambda 4$ and $\lambda 5$ is set or a larger K is set. For example, the detection width can be enlarged (for example, to 10 nm or more) as a larger difference between $\lambda 4$ and $\lambda 4$ is set or a smaller K is set. For example, the detection width can be set to be large by taking an average of output values at two or more pixels.

The light detector 27 captures an image of a linear part of the tissue BT that is disposed in the lighting region IR by single imaging processing. In the present embodiment, the stage device 21 is movable in a predetermined direction while holding the tissue BT, so that the relative positions between the lighting region IR and the tissue BT can be changed. When the stage device 21 moves in the Y-axis direction while holding the tissue BT, the relative positions between the lighting region IR and the tissue BT change in the Y-axis direction, and the tissue BT is scanned with light from the light source 25. The controller 23 controls the imaging apparatus 2 to repeatedly execute imaging processing while moving the stage device 21 holding the tissue BT in the Y-axis direction, thereby acquiring a two-dimensional image of the tissue BT.

The controller 23 includes an image analyzer 24 and a storage 30. The image analyzer 24 analyzes a captured image obtained by capturing an image of the tissue BT, and detects substances included in the tissue BT. For example, the image analyzer 24 uses a hyperspectral image (a plurality of sample images) captured by the imaging apparatus 2 to analyze optical properties (for example, spectral properties) of the biological tissue BT. In the present embodiment, the controller 23 stores various kinds of information, such as sample images acquired from the imaging apparatus 2, in the storage 30. The image analyzer 24 reads various kinds of information from the storage 30 and processes the information.

Figure 13A:
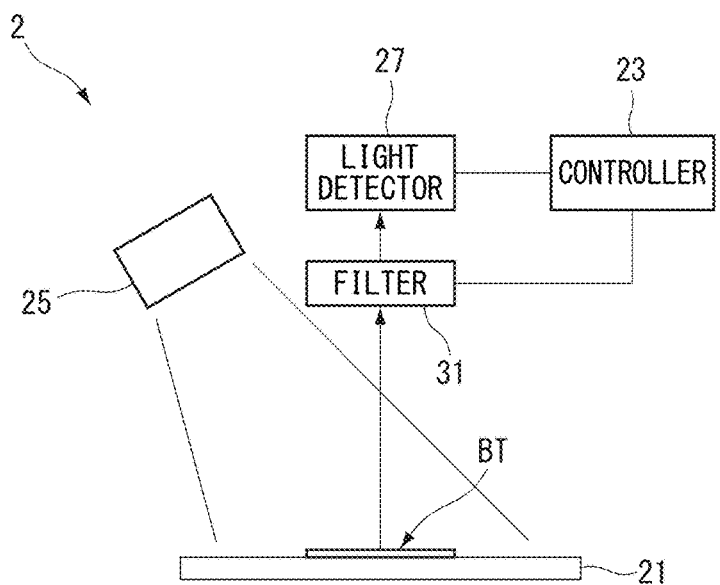
FIGS. 13A and 13B are each a diagram showing another configuration of the imaging apparatus.
Figure 13B:
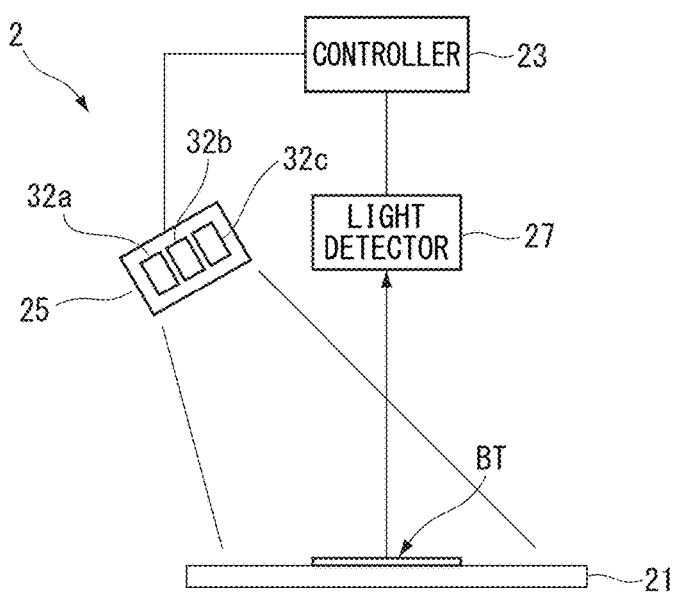

While in the present embodiment, the imaging apparatus 2 disperses light radiated from the tissue BT to acquire a hyperspectral image, the imaging apparatus 2 may employ another configuration. For example, the imaging apparatus 2 may be configured to acquire data (for example, sample data) while switching the wavelength bandwidth of light output from the light source 25. Examples of the method of acquiring a hyperspectral image in the present embodiment include spatial scanning, spectrum scanning, Fourier transform, and interference filtering. FIGS. 13A and 13B are each a diagram showing another configuration of the imaging apparatus 2. The controller 23 has the same configuration as in the above, and the image analyzer 24 can generate analysis image data by using sample data from the imaging apparatus 2.

The imaging apparatus 2 shown in FIG. 13A includes a light source 25, a filter 31, and a light detector 27. The light source 25 outputs infrared light having a wide wavelength bandwidth corresponding to a predetermined wavelength bandwidth. The filter 31 is disposed in an optical path between the light source 25 and the light detector 27. For example, the filter 31 is provided in at least one of an optical path between the light source 25 and the tissue BT and an optical path between the tissue BT and the light detector 27. The filter 31 includes a plurality of filters, and the plurality of filters transmit infrared light having different wavelengths. The filter 31 is driven by a driver (not shown), and can switch a filter disposed between the light source 25 and the light detector 27 among the plurality of filters.

The controller 23 controls a driver for the filter 31 to switch a filter disposed in an optical path between the light source 25 and the light detector 27, thereby controlling the wavelength of infrared light entering the light detector 27. For example, the controller 23 disposes a first filter that transmits infrared light having a first wavelength band in the optical path between the light source 25 and the light detector 27. The controller 23 controls the light detector 27 to capture an image of the tissue BT in a period during which the infrared light having the first wavelength band radiated from the tissue BT enters the light detector. The controller 23 acquires a spatial distribution of light intensity of the infrared light having the first wavelength band radiated from the tissue BT on the basis of the capture result of the light detector 27. Similarly, the controller 23 disposes a second filter that transmits infrared light having a second wavelength band in the optical path between the light source 25 and the light detector 27, and a spatial distribution of light intensity of the infrared light having the second wavelength band radiated from the tissue BT. In this manner, the controller 23 is capable of generating sample data in N wavelength bands.

The imaging apparatus 2 shown in FIG. 13B includes a light source 25 and a light detector 27. The light source 25 includes a light source 32a that outputs infrared light having a first wavelength band, a light source 32b that outputs infrared light having a second wavelength band, and a light source 32c that outputs infrared light having a third wavelength band. The controller 23 controls turning-on and turning-off of each of the light source 32a, the light source 32b, and the light source 32c. The controller 23 turns on the light source 32a and turns off the light source 32b and the light source 32c. In this manner, infrared light having the first wavelength band is output from the light source 25, and infrared light having the first wavelength band radiated from the tissue BT enters the light detector 27. The controller 23 controls the light detector 27 to capture an image of the tissue BT while switching a turned-on light source among the light source 32a, the light source 32b, and the light source 32c. In this manner, the controller 23 can acquire sample image in each of a plurality of wavelength bands. The above-described infrared light beams having the first to third wavelength bands (in this case, three infrared light beams) include light having a wavelength band selected from the above-described analysis wavelength band on the basis of the Nth-order derivative. The imaging system 20 in the present embodiment includes a light source 25 that is capable of outputting at least three infrared light beams having different wavelengths (light beams in three infrared bandwidths) to the tissue BT, a light detector 27 that receives the three infrared light beams via the tissue BT, and the above-described image analysis apparatus 1. The image analysis apparatus 1 includes a distribution data generator 3 that generates, on the basis of a sample image obtained from the light detector 27, distribution data indicating a spectrum of the tissue BT in the three infrared light beams, a differential calculator 4 that calculates, on the basis of the distribution data, an Nth-order derivative (N is an integer of 2 or more) of the spectrum, and an image data generator 5 that converts the Nth-order derivative into a gray-scale value to generate image data. The image analysis apparatus 1 or the imaging system 20 in the present embodiment can visualize a distribution of a predetermined substance in the tissue BT as an image with high accuracy. The above-described three infrared light beams are selected from the above-described analysis wavelength band. In the visualization, the image analysis apparatus 1 may display a predetermined substance in the tissue BT in an emphasized manner by multiple colors based on the gray-scale values.

[Pathological Analysis System]

Figure 14:
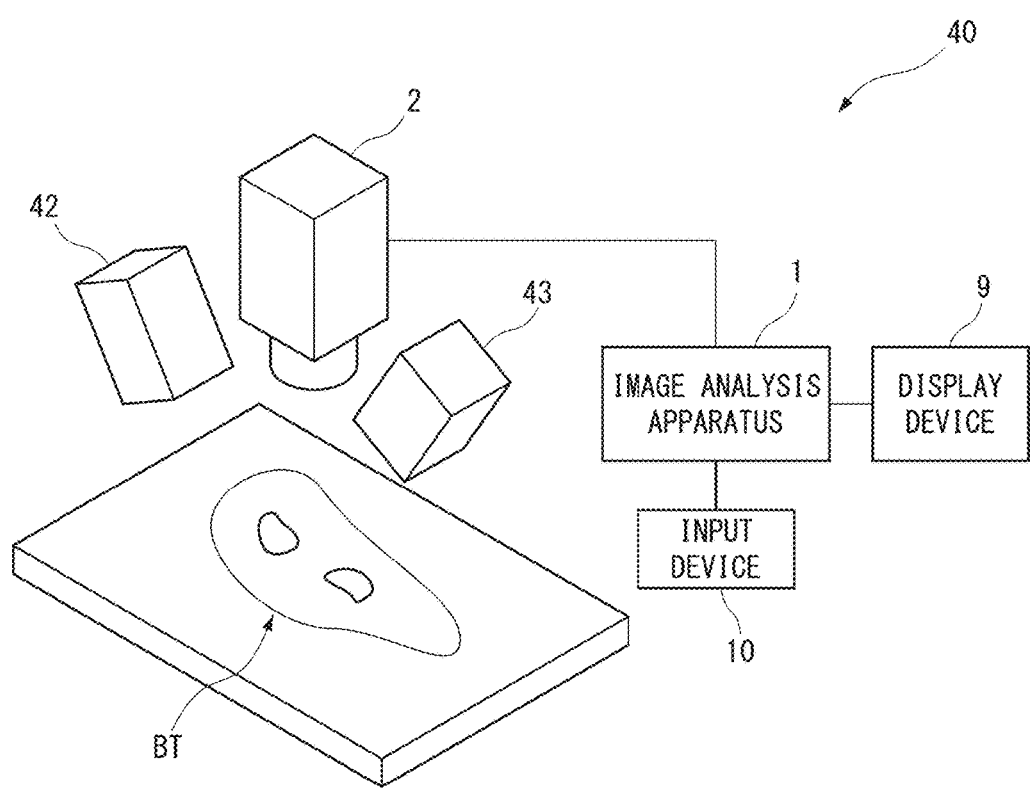
FIG. 14 is a diagram showing an example of a pathological analysis system according to the present embodiment.

Next, a pathological analysis system (medical support system) will be described. FIG. 14 is a diagram showing an example of a pathological analysis system 40. The pathological analysis system 40 includes a table 41, an irradiator 42, an irradiator 43, an imaging apparatus 2, an image analysis apparatus 1, an input device 10, and a display device 9. A tissue BT can be placed on the top surface of the table 41. The irradiator 42 irradiates a tissue BT on the table 41 with, for example light in an infrared bandwidth. The irradiator 43 irradiates the tissue BT on the table 41 with, for example, light in a visible bandwidth. The imaging apparatus 2 can capture an infrared image and a visible image. For example, as shown in FIG. 13, the irradiator 42 and the imaging apparatus 2 are configured to switch the wavelength of light detected by the imaging apparatus 2.

The image analysis apparatus 1 generates data on an analysis image indicating a distribution of a predetermined substance in a tissue BT on the basis of a sample image captured by the imaging apparatus 2. The image analysis apparatus 1 supplies the data on the analysis image to the display device 9, and displays the analysis image on the display device 9. For example, the image analysis apparatus can display a first distribution image indicating a distribution of a first predetermined substance in the tissue BT and a second distribution image indicating a distribution of a second predetermined substance in the tissue BT on the display device 9 while switching between the first distribution image and the second distribution image.

The image analysis apparatus 1 can display a visible light image captured by the imaging apparatus 2 on the display device 9. The image analysis apparatus 1 can display an overlay image, in which a visible light image captured by the imaging apparatus 2 and an image indicating analysis results are overlaid, on the display device 9. For example, the user can make a pathological diagnosis while viewing an image displayed on the display device 9.

[Surgery Support System]

Figure 15:
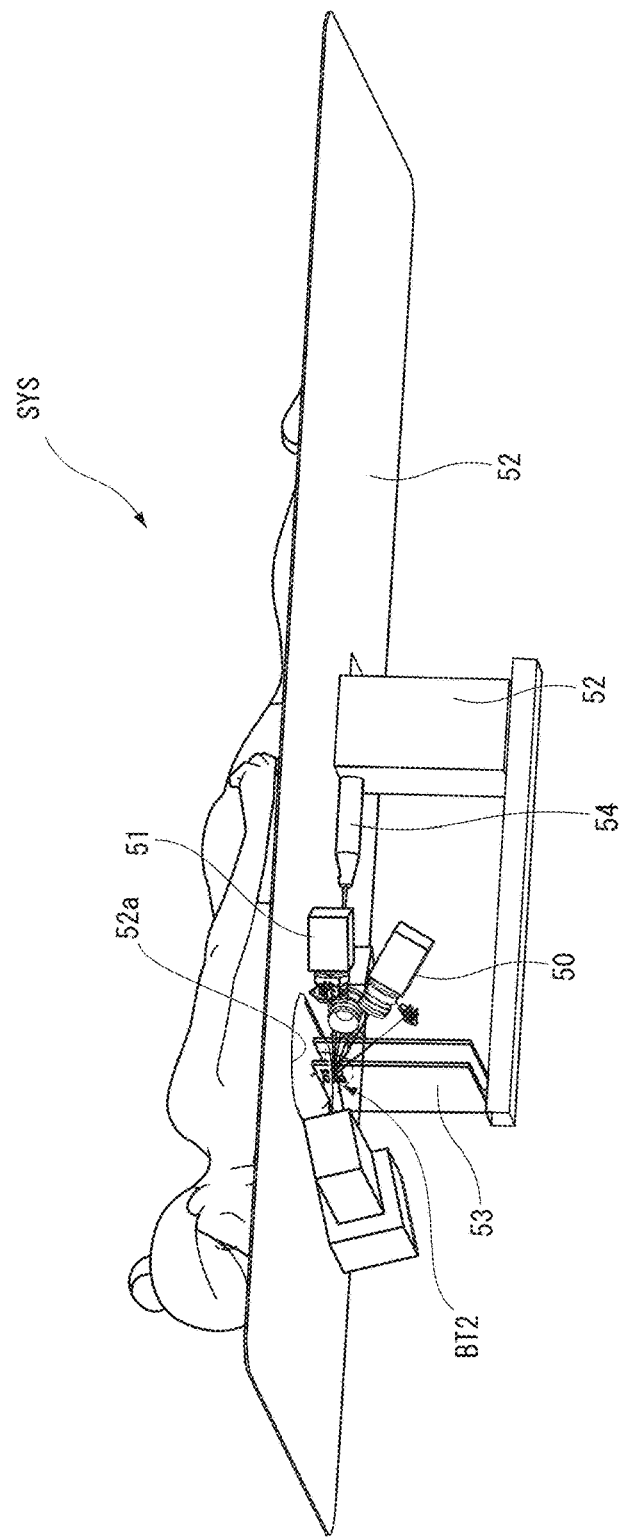
FIG. 15 is a diagram showing an example of a surgery support system SYS according to the present embodiment.

Next, a surgery support system (medical support system) will be described. FIG. 15 is a diagram showing an example of a surgery support system SYS. The surgery support system SYS is a mammotome using the image analyzer described in the above-described embodiments. The surgery support system SYS includes a lighting device 50 and an infrared camera 51. The lighting device 50 irradiates a tissue such as a breast with detection light. The infrared camera 51 is a light detector that detects light radiated from the tissue. An image analyzer (not shown) (image analysis apparatus 1) generates analysis image data on the basis of the detection result (sample data) of the infrared camera 51.

The surgery support system SYS also includes a bed 52, a transparent plastic plate 53, and a perforation needle 54. The bed 52 is a bed on which an examinee lies with his or her face down. The bed 52 has an aperture 52a through which a breast BT2 (tissue) of the examinee as the subject is exposed downward. The transparent plastic plate 53 is used to sandwich both sides of the breast BT2 to flatten the breast BT2. The perforation needle 54 is an operation device capable of treating the tissue. The perforation needle 54 is inserted into the breast BT2 in a core needle biopsy to take a sample.

As shown in FIG. 15, the breast BT2 is flattened by pressing the transparent plastic plate 53 against both sides thereof, and in this state, the lighting device 50 outputs infrared light having a predetermined wavelength band so that the infrared camera 51 captures an image. In this manner, the infrared camera 51 acquires an image of the breast BT2 with infrared light reflected from the lighting device 50.

In a general core needle biopsy, a perforation needle (core needle) is inserted while measuring the depth of the needle using ultrasonic echo. A breast generally includes tissues with a large amount of lipid, but when a breast cancer occurs, the amount of water in the breast cancer area may differ from that in other areas.

The surgery support system SYS can generate an image indicating a distribution of a predetermined substance in the breast BT2 by the above-described image analysis apparatus, and insert the perforation needle 54 into the breast BT2 to take a tissue while projecting the image on a patient tissue (for example, the breast BT2) or displaying the image on a display. For example, an operator can insert the perforation needle 54 into a part of the breast BT2 where the amount of water is different from those in other parts while observing an analysis image generated by the image analysis apparatus. Such a surgery support system SYS can take a sample while accurately analyzing the distribution of a training substance in the tissue. Imaging with infrared light, which does not cause X-ray exposure, can be usually used in obstetrics and gynecology, regardless of whether the patient is pregnant. In this manner, for example, the surgery support system SYS includes the imaging system 20 including the image analyzer 24, and an operation device such as a perforation needle 54.

Next, another surgery support system (medical support system) will be described. In the present embodiment, the same configuration as in the above-described embodiments is denoted by the same reference symbol and description thereof is simplified or omitted.

Figure 16:
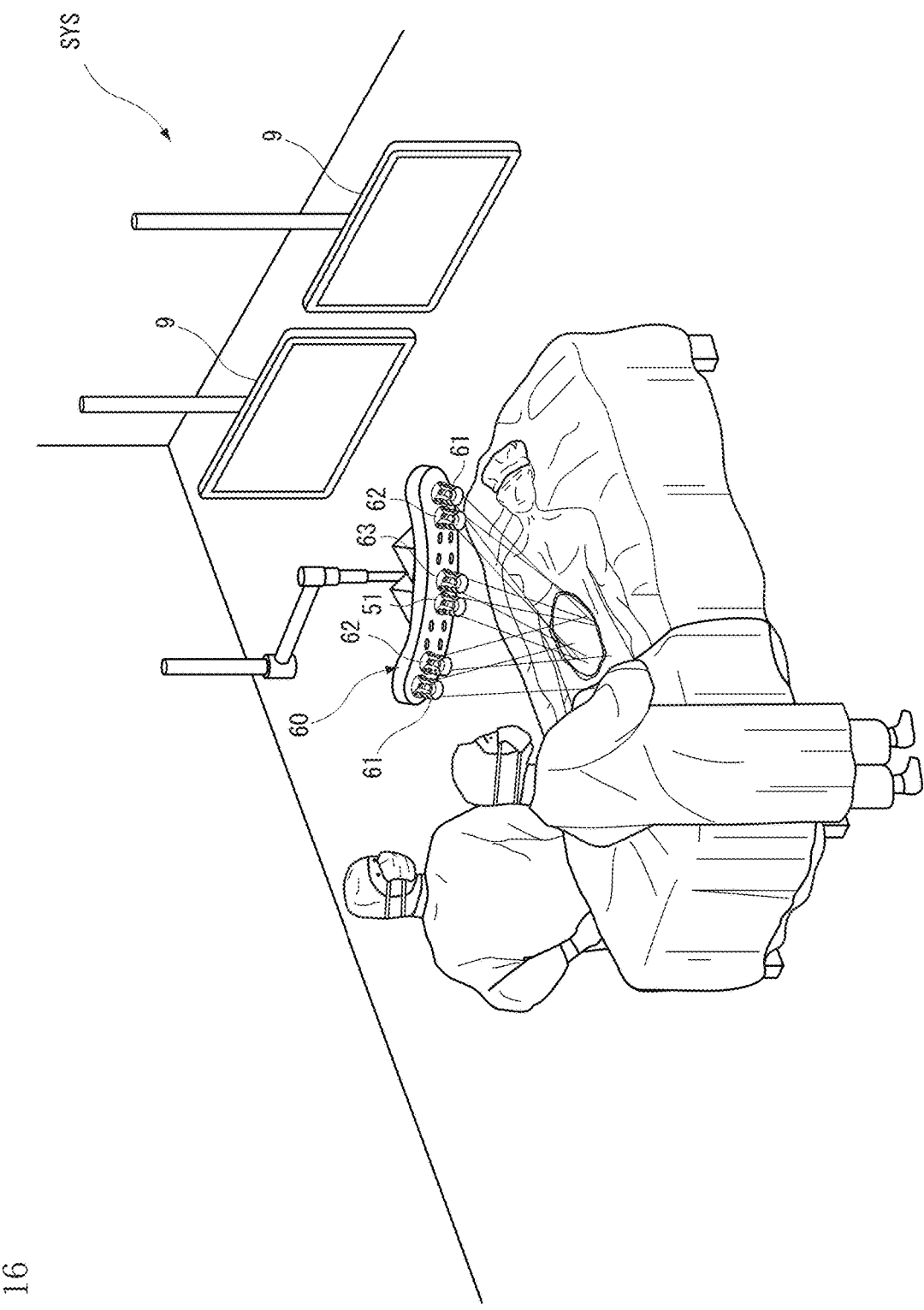
FIG. 16 is a diagram showing another example of the surgery support system SYS according to the present embodiment.

Next, another example of the surgery support system is described. FIG. 16 is a diagram showing another example of the surgery support system SYS. The surgery support system SYS is used for a laparotomy or other operations. The surgery support system SYS includes an operation device (not shown) capable of treating a tissue to be treated in a state in which an image about the tissue is projected on the tissue. For example, the operation device includes at least one of a blood sampling device, a hemostatic device, a laparoscopic device including endoscopic and other instruments, an incisional device, and an abdominal operation device.

The surgery support system SYS includes a surgery lamp 60 and two display devices 9. The surgery lamp 60 includes visible lighting lamps 61 that output visible light, infrared LED modules 62, an infrared camera 51, and a projector 63. The infrared LED modules 62 irradiate a tissue exposed in laparotomy with detection light. The infrared camera 51 is a light detector that detects light radiated from the tissue. The projector 63 can project an image generated by the controller (not shown) by using the detection result of the infrared camera 51 (captured image). The display devices 9 can display an image acquired by the infrared camera 51 and a component image generated by the controller. For example, a visible light camera is provided to the surgery lamp 60, and the display devices 9 can also display an image acquired by the visible light camera. The display devices 9 can display an image generated by the image analysis apparatus 1 using infrared light and an image acquired by the visible light camera in a superimposed manner.

The invasiveness and efficiency of an operation or treatment are determined by the range and intensity of injury or cautery associated with incision and hemostasis. The surgery support system SYS projects an image indicating information on a tissue on the tissue. Thus, a legion, as well as nerves, solid organs such as pancreas, fat tissue, blood vessels, and the like can be easily recognized to reduce invasiveness of an operation or treatment and enhance the efficiency of an operation or treatment.

The technical scope of the present invention is not limited to the above-described embodiments or modifications. For example, one or more elements described in the above-described embodiments or modifications may be omitted. The elements described in the above-described embodiments or modifications can be combined as appropriate.

DESCRIPTION OF REFERENCE SIGNS

1 . . . image analysis apparatus, 2 . . . imaging apparatus, 3 . . . distribution data generator, 4 . . . differential calculator, 5 . . . image data generator, 11 . . . extractor, 20 . . . imaging system, 24 . . . image analyzer, BT . . . tissue, SYS . . . surgery support system

What is claimed is:

1. An image analysis apparatus comprising:
a distribution data generator, of a computer, that generates, on the basis of a sample image obtained by irradiating a tissue including a part containing water and a part containing lipid with light having an infrared bandwidth, distribution data indicating a distribution of light intensity in the infrared bandwidth in at least the part containing water in the tissue;
a differential calculator, of a computer, that calculates, on the basis of the distribution data, an Nth-order derivative of the distribution of the light intensity in a first wavelength band in the infrared bandwidth, where N is an integer of 2 or more, for each region in the sample image; and
an image data generator, of a computer, that converts the calculated Nth-order derivative into a gray-scale value to generate image data in which the part containing water is emphasized.

2. The image analysis apparatus of claim 1, wherein the first wavelength band is set to a wavelength band that includes a non-linear part of the distribution of the light intensity.

3. The image analysis apparatus of claim 1, wherein the first wavelength band is set to a wavelength band that includes a local maximum value or a local minimum value of the distribution of the light intensity.

4. The image analysis apparatus of claim 1, wherein the distribution data generator generates the distribution data for each region in the sample image.

5. The image analysis apparatus of claim 1, wherein the first wavelength band is selected on the basis of a spectrum of a predetermined substance contained in the tissue.

6. The image analysis apparatus of claim 5, wherein the predetermined substance comprises lipid or water.

7. The image analysis apparatus of claim 1, wherein the distribution data generator generates the distribution data by using at least three wavelengths in the first wavelength band.

8. The image analysis apparatus of claim 1, wherein the first wavelength band is set to 900 nm or more and 1700 nm or less.

9. The image analysis apparatus of claim 1, wherein
the distribution data generator generates, as the distribution data, discrete data that includes light intensity for each of M wavelengths, where M is an integer larger than the N by 1 or more, in a wavelength band including the first wavelength band, and
the differential calculator uses a difference in light intensity included in the distribution data to calculate an Nth-order derivative in the first wavelength band.

10. The image analysis apparatus of claim 1, wherein
the distribution data generator calculates a continuous function indicating a distribution of the light intensity in a wavelength band including the first wavelength band, and
the differential calculator uses the continuous function to calculate an Nth-order derivative in the first wavelength band.

11. The image analysis apparatus of claim 1, wherein the differential calculator calculates, on the basis of the distribution data generated by the distribution data generator, an Nth-order derivative of a distribution of the light intensity in each of a plurality of wavelengths in the infrared bandwidth for each region in the sample image.

12. The image analysis apparatus of claim 11, comprising an extractor, of a computer, that uses an Nth-order derivative calculated by the differential calculator for each of the plurality of wavelengths to extract a wavelength band in which an absolute value of the Nth-order derivative is a threshold or more.

13. An imaging system comprising:
the image analysis apparatus of claim 1; and
an imager that acquires the sample image in the tissue.

14. The imaging system of claim 13, comprising a display that displays an image by using the image data generated by the image data generator.

15. An imaging system comprising:
a light source capable of outputting at least three infrared light beams having different wavelengths to a tissue including a part containing water and a part containing lipid;
a light detector that receives the three infrared light beams via the tissue; and
an image analysis apparatus,
the image analysis apparatus comprising:
a distribution data generator, of a computer, that generates, on the basis of a sample image obtained from the light detector, distribution data indicating a spectrum of the tissue with the three infrared light beams;
a differential calculator, of a computer, that calculates an Nth-order derivative (N is an integer of 2 or more) of the spectrum on the basis of the distribution data; and
an image data generator, of a computer, that converts the calculated Nth-order derivative into a gray-scale value to generate image data in which the part containing water is emphasized.

16. A surgery support system comprising:
the imaging system of claim 13; and
an operation device that is capable of treating the tissue.

17. A non-transitory storage medium storing therein an image analysis program that causes a computer to execute:
generating, on the basis of a sample image obtained by irradiating a tissue including a part containing water and a part containing lipid with light having an infrared bandwidth, distribution data indicating a distribution of light intensity in the infrared bandwidth in at least the part containing water in the tissue;
calculating, on the basis of the distribution data, an Nth-order derivative of a distribution of the light intensity in a first wavelength band in the infrared bandwidth, where N is an integer of 2 or more, for each region in the sample image; and
converting the calculated Nth-order derivative into a gray-scale value to generate image data in which the part containing water is emphasized.

18. An image analysis apparatus comprising:
a data generator, of a computer, that generates, on the basis of a detection result obtained by irradiating a target including a first part containing water and a second part containing lipid with infrared light, spectrum data indicating a spectrum of the target;
a differential calculator, of a computer, that calculates, on the basis of the spectrum data, a first Nth-order derivative (N is an integer of 2 or more) of a spectrum in a first predetermined wavelength band that includes a non-linear part of the spectrum, for each of the first part and the second part and that calculates, on the basis of the spectrum data, a second Nth-order derivative (N is an integer of 2 or more) of a spectrum in a second predetermined wavelength band that includes a non-linear part of the spectrum, for each of the first part and the second part; and
an image data generator, of a computer, that converts the calculated first Nth-order derivative into a gray-scale value to generate image data in which the first part is emphasized and that converts the calculated second Nth-order derivative, into a gray-scale value to generate image data in which the second part is emphasized.

19. The image analysis apparatus of claim 18, wherein the image data generator converts the first Nth-order derivative into a gray-scale value to generate image data in which the first part is emphasized more than the second part or converts the second Nth-order derivative into a gray-scale value to generate image data in which the second part is emphasized more than the first part.

20. The image analysis apparatus of claim 18, wherein the first predetermined wavelength band and the second predetermined wavelength band each comprise at least a part of a wavelength band from 900 nm or more to 2000 nm or less.

21. The image analysis apparatus of claim 18, wherein the first predetermined wavelength band and the second predetermined wavelength band are each selected on the basis of a spectrum of the water and a spectrum of the lipid.

22. The image analysis apparatus of claim 18, wherein the detection result comprises a hyperspectral image.

23. A detection system comprising:
the image analysis apparatus of claim 18; and
a detector that acquires the detection result.

24. A surgery support system comprising:
the detection system of claim 23; and
a display that displays the image data.

25. A non-transitory storage medium storing therein a program that causes a computer to execute:
generating, on the basis of a detection result obtained by irradiating a target including a first part containing water and a second part containing lipid with infrared light, spectrum data indicating a spectrum of the target;
calculating, for each of the first part and the second part, on the basis of the spectrum data, a first Nth-order derivative (where N is an integer of 2 or more) of a spectrum in a first predetermined wavelength band including a non-linear part of the spectrum and calculating, for each of the first part and the second part, on the basis of the spectrum data, a second Nth-order derivative (where N is an integer of 2 or more) of a spectrum in a second predetermined wavelength band including a non-linear part of the spectrum;
converting the calculated first Nth-order derivative into a gray-scale value to generate image data in which the first part is emphasized; and
converting the calculated second Nth-order derivative, into a gray-scale value to generate image data in which the second part is emphasized.

26. The image analysis apparatus of claim 18, wherein the differential calculator calculates the first Nth-order derivative by using light intensities with respect to at least three wavelengths in the first predetermined wavelength band in the spectrum data.

27. The image analysis apparatus of claim 18, wherein the differential calculator calculates the second Nth-order derivative by using light intensities with respect to at least three wavelengths in the second predetermined wavelength band in the spectrum data.

28. The image analysis apparatus of claim 1, wherein the differential calculator calculates the Nth-order derivative by Nth-order differential processing of the distribution of the light intensity in the first wavelength band in the infrared bandwidth.

29. The image analysis apparatus of claim 1, wherein
the part containing water is a part in which a proportion of water is larger than that in the part containing lipid, and
the part containing lipid is a part in which a proportion of lipid is larger than that in the part containing water.

30. The image analysis apparatus of claim 1, wherein the image data generator generates the image data in which the part containing water is emphasized as being represented by a dark part or a bright part based on the gray-scale value.

* * * * *